US009226799B2

(12) United States Patent
Lightcap et al.

(10) Patent No.: US 9,226,799 B2
(45) Date of Patent: Jan. 5, 2016

(54) INERTIALLY TRACKED OBJECTS

(75) Inventors: Chris Lightcap, Davie, FL (US); Hyosig Kang, Weston, FL (US)

(73) Assignee: MAKO Surgical Corp., Fort Lauderdale, FL (US)

( * ) Notice: Subject to any disclaimer, the term of this patent is extended or adjusted under 35 U.S.C. 154(b) by 233 days.

(21) Appl. No.: 12/821,365

(22) Filed: Jun. 23, 2010

(65) Prior Publication Data

US 2011/0320153 A1 Dec. 29, 2011

(51) Int. Cl.
*A61B 19/00* (2006.01)
*A61B 17/00* (2006.01)

(52) U.S. Cl.
CPC ... *A61B 19/5244* (2013.01); *A61B 2017/00477* (2013.01); *A61B 2017/00725* (2013.01); *A61B 2017/00876* (2013.01); *A61B 2019/4894* (2013.01); *A61B 2019/527* (2013.01); *A61B 2019/5248* (2013.01); *A61B 2019/5259* (2013.01); *A61B 2019/5268* (2013.01)

(58) Field of Classification Search
CPC .................... A61B 19/5244; A61B 2017/0047
USPC .............................. 702/94; 600/426; 606/130
See application file for complete search history.

(56) References Cited

U.S. PATENT DOCUMENTS

| 5,645,077 | A | 7/1997 | Foxlin |
| 6,322,567 | B1 | 11/2001 | Mittelstadt et al. |
| 6,361,507 | B1 | 3/2002 | Foxlin |
| 6,681,629 | B2 | 1/2004 | Foxlin et al. |
| 7,301,648 | B2 | 11/2007 | Foxlin |
| 2006/0058604 | A1 | 3/2006 | Avinash et al. |
| 2006/0142657 | A1 | 6/2006 | Quaid et al. |
| 2008/0004633 | A1 | 1/2008 | Arata et al. |
| 2008/0039868 | A1* | 2/2008 | Tuemmler et al. ............ 606/130 |
| 2009/0024044 | A1 | 1/2009 | Virtanen et al. |
| 2009/0306499 | A1* | 12/2009 | Van Vorhis et al. ........... 600/426 |
| 2009/0314925 | A1 | 12/2009 | Van Vorhis et al. |
| 2010/0166496 | A1 | 7/2010 | Bennett et al. |
| 2012/0277634 | A1* | 11/2012 | Proulx et al. .................. 600/595 |

FOREIGN PATENT DOCUMENTS

DE 10-2006-032127 1/2008

OTHER PUBLICATIONS

Ang, et al., "Active Tremor Compensation in Microsurgery," *Proceedings of the 26th Annual International Conference of the IEEE EMBS*, pp. 2738-2741 (Sep. 1-5, 2004).
Ang, et al., "Design of All-Accelerometer Inertial Measurement Unit for Tremor Sensing in Hand-held Microsurgical Instrument," *IEEE International Conference on Robotics and Automation*, pp. 1781-1786 (Sep. 2003).
Bandala, et al., "Wireless inertial sensor for tumour motion tracking," Journal of Physics: Conference Series 76, pp. 1-6 (2007).
International Search Report PCT Application No. PCT/US2010/039620, mailed on Mar. 21, 2011 (3 pgs.).

* cited by examiner

*Primary Examiner* — Toan Le
*Assistant Examiner* — Manuel Rivera Vargas
(74) *Attorney, Agent, or Firm* — Foley & Lardner LLP

(57) ABSTRACT

Described are computer-based methods and apparatuses, including computer program products, for inertially tracked objects with a kinematic coupling. A tracked pose of a first inertial measurement unit (IMU) is determined, wherein the first IMU is mounted to a first object. The tracked pose of the first IMU is reset while the first object is in a first reproducible reference pose with a second object.

21 Claims, 13 Drawing Sheets

INERTIALLY TRACKED OBJECTS

FIELD OF THE INVENTION

The present invention relates generally to computer-based methods and apparatuses, including computer program products, for inertially tracked objects.

BACKGROUND

Orthopedic joint replacement surgery may involve arthroplasty of a knee, hip, or other joint (e.g., shoulder, elbow, wrist, ankle, finger, etc.). During joint replacement surgery, a surgeon typically removes diseased bone from the joint and replaces the resected bone with prosthetic implant components. Challenges of joint replacement surgery include determining the appropriate position for implant components within the joint relative to the bone and other implant components and accurately cutting and reshaping bone to precisely correspond to the planned placement of the implant components. Inaccurate positioning of implants may compromise joint performance and reduce implant life.

A surgical system for joint replacement surgery can include a haptic device configured to be manipulated by a surgeon to guide a surgical cutting tool to perform a procedure on a patient. For example, a surgeon can manipulate the haptic device to sculpt a bone so that an implant component can be installed on the sculpted bone. Prior to surgery, a three dimensional model of the bone is created using software techniques. The software model is used to generate a surgical plan, that includes, for example, resecting bone (e.g., using the surgical cutting tool) and inserting implant components. During surgery, the surgeon manipulates the haptic device to move the surgical tool to cut bone, and the haptic device provides force feedback to prevent the surgeon from moving the surgical tool in a way that does not conform with the surgical plan. For example, if the surgeon's movement of the haptic device would cause the surgical tool to resect too much of the patient's bone, the haptic device can apply resistance against the surgeon's movement to prevent the resection. A navigation or tracking system can be used to determine a pose (i.e., position and/or orientation) of the bone, the haptic device, the surgical tool, and/or other objects of interest. As is well known, pose data from the tracking system can be used for registration and real-time object tracking.

For example, U.S. patent application Ser. No. 11/357,197 (U.S. Pub. No. 2006/0142657), which is hereby incorporated by reference herein in its entirety, describes that objects in physical space (e.g., anatomy, surgical tools, etc.) may be registered to any suitable coordinate system, such as a coordinate system being used by a process running on a computer associated with a surgical system. For example, utilizing object pose data captured by a tracking system, the surgical system can associate the physical anatomy and the surgical tool with a representation of the anatomy (such as a computer-generated three-dimensional model or image of the anatomy). Based on the tracked object and registration data, the surgical system can determine, for example, (a) a spatial relationship between the image of the anatomy and the relevant physical anatomy and (b) a spatial relationship between the relevant physical anatomy and the surgical tool so that the computing system can superimpose (and continually update) a virtual representation of the tool on the image of the anatomy, where the relationship between the virtual representation of the tool and the image of the anatomy is substantially identical to the relationship between the actual surgical tool and the physical anatomy. Additionally, by tracking not only the tool but also the relevant anatomy, the surgical system can compensate for movement of the relevant anatomy during the surgical procedure (e.g., by adjusting a virtual object that defines a surgical cutting boundary in response to the detected movement of the anatomy).

The tracking system enables the surgical system to determine (or track) in real-time a pose of tracked objects, such as the bone. One common type of tracking system is an optical tracking system that includes an optical camera configured to locate in a predefined coordinate space specially recognizable markers (e.g., LEDs or reflective spheres) that are attached to the tracked object. However, optical tracking systems require a direct line of sight between the optical camera and the markers. This restricts the movement of the surgeon during surgery because the surgeon cannot interfere with the optical communication between the optical camera and the markers. As a result, the surgeon's movement is limited not only by the location of physical equipment in the operating room but also by lines of sight between the optical camera and markers. Further, other unavoidable surgical side-effects can interfere with the optical communication, such as bone debris that is generated during a bone resection and occludes the surface of one or more markers. Additionally, while optical tracking systems are often accurate, they can be cost-prohibitive.

Another type of tracking system is an inertial tracking system, which uses an inertial measurement unit (IMU) to track an object. An IMU is an electronic device that includes a combination of accelerometers and/or gyroscopes to measure characteristics of an object, such as the object's velocity, orientation, and/or gravitational forces. For example, an IMU can measure three degrees of freedom of the acceleration and three degrees of freedom of the angular rate of the IMU. Using these measurements, the inertial tracking system can estimate the current six degree of freedom pose of the IMU based on a previously determined IMU pose (e.g., an initial (or starting) reference pose) and changes in acceleration and angular rate of the IMU over time. While inertial tracking systems can be more cost-effective than other tracking systems, in general inertial tracking systems introduce greater error through drift. That is, since new poses are calculated from previously determined poses and measured changes in acceleration and angular rate (without reference to any external references), the errors of the tracking process are cumulative such that the error in each new estimated IMU pose grows with time. Specifically, the inertial tracking system integrates the linear accelerations and angular velocities provided by the IMU to calculate the new IMU pose (the acceleration data is often double integrated). The accumulated error leads to "drift," or an ever-increasing difference between where the inertial tracking system thinks the IMU is located and the actual IMU pose. If the drift is not compensated for, the pose of the tracked object (e.g., the bone) can be incorrectly predicted based on the difference between the predicted IMU pose and the actual IMU pose. This could cause the surgical system to be improperly configured unbeknownst to the surgeon, which could lead to the surgical plan being carried out improperly (e.g., performing improper resections).

In view of the foregoing, a need exists for methods and devices which can overcome the aforementioned problems so as to enable computer assisted surgery (CAS) to be carried out when drift occurs between an IMU's calculated pose and actual pose by resetting a reference pose of the IMU.

SUMMARY OF THE INVENTION

The techniques described herein provide surgical systems and methods for inertially tracking objects and eliminating drift associated with the tracked objects by resetting the reference pose of the inertial tracker(s) mounted to the tracked objects. A reproducible reference pose is established between the tracked objects such that the tracked objects can be repeatedly and accurately placed into the reproducible reference pose to reset a tracking calculation between the objects. When the drift associated with an inertial tracker mounted to one (or more) of the tracked objects becomes too large, the tracked objects can be placed into the reproducible reference pose to reset the reference pose of the inertial tracker(s). Advantageously, a cost-effective inertial tracking system can be deployed that not only eliminates drift but also avoids disadvantages associated with other tracking systems. For example, optical tracking systems are often more expensive than inertial tracking systems and the surgeon's movement is often restricted to maintain a line of sight between the markers and the optical camera.

In one aspect, there is a method of resetting a tracking element. The method includes determining, by an inertial tracking system, a tracked pose of a first inertial measurement unit (IMU), wherein the first IMU is mounted to a first object. The method includes resetting, by the inertial tracking system, the tracked pose of the first IMU while the first object is in a first reproducible reference pose with a second object.

In another aspect, there is a method for inertially tracking one or more objects. The method includes determining, by an inertial tracking system, that an error associated with a first IMU, a second IMU, or both, exceeds a predetermined threshold, wherein the error is indicative of a first discrepancy between a tracked pose of the first IMU and an actual pose of the first IMU, a second discrepancy between a tracked pose of the second IMU and an actual pose of the second IMU, or both. The method includes resetting the tracked pose of the first IMU, the tracked pose of the second IMU, or both, based on a reproducible reference pose, wherein the reproducible reference pose includes a predetermined transformation indicative of a first pose of the second IMU with respect to a first pose of the first IMU, including setting the tracked pose of the first IMU to the first pose of the first IMU, or setting the tracked pose of the second IMU to the first pose of the second IMU, or both.

In a further aspect, there is a computer program product. The computer program product is tangibly embodied in a computer readable storage medium. The computer program product includes instructions being operable to cause a data processing apparatus to determine a tracked pose of a first inertial measurement unit (IMU), wherein the first IMU is mounted to a first object. The computer program product includes instructions being operable to cause a data processing apparatus to reset the tracked pose of the first IMU while the first object is in a first reproducible reference pose with a second object.

In another aspect, there is an apparatus for inertially tracking one or more objects. The apparatus includes an inertial tracking system configured to determine a tracked pose of a first inertial measurement unit (IMU), wherein the first IMU is mounted to a first object. The inertial tracking system is configured to reset the tracked pose of the first IMU while the first object is in a first reproducible reference pose with a second object.

In a further aspect, there is an apparatus for inertially tracking one or more objects. The apparatus includes a means for determining a tracked pose of a first inertial measurement unit (IMU), wherein the first IMU is mounted to a first object and resetting the tracked pose of the first IMU while the first object is in a first reproducible reference pose with a second object.

In other examples, any of the aspects above can include one or more of the following features. The first IMU can include a first coupling configured to couple to a second coupling mounted to the second object to achieve the first reproducible reference pose.

In some examples, the inertial tracking system determines a tracked pose of a second IMU, wherein the second IMU is mounted to the second object. The inertial tracking system can reset the tracked pose of the second IMU while the first object is in the first reproducible reference pose with the second object. Resetting the tracked pose of the first IMU and resetting the tracked pose of the second IMU can include determining the first object and the second object are in the first reproducible reference pose, and resetting the tracked pose of at least one of the first IMU and the second IMU based on the first reproducible reference pose.

In other examples, the first reproducible reference pose includes a predetermined transformation indicative of a first pose of the second IMU with respect to a first pose of the first IMU. A tracked pose of the second IMU can be determined with respect to the first IMU based on the tracked pose of the first IMU, the tracked pose of the second IMU, and the first reproducible reference pose. The first IMU can include a first kinematic coupling and the second IMU includes a second kinematic coupling. The first kinematic coupling can be configured to kinematically couple to the second kinematic coupling to achieve the first reproducible reference pose. The tracked pose of the first IMU, the tracked pose of the second IMU, or both, can be reset when the second kinematic coupling is kinematically coupled to the first kinematic coupling.

In some examples, the inertial tracking system determines that an error associated with the first IMU, the second IMU, or both, exceeds a predetermined threshold. The tracked pose of the first IMU, the tracked pose of the second IMU, or both, are reset based on the first reproducible reference pose. The first reproducible reference pose can include a predetermined transformation indicative of a first pose of the second IMU with respect to a first pose of the first IMU, and resetting the tracked pose of the first IMU and resetting the tracked pose of the second IMU can include setting the tracked pose of the first IMU to the first pose of the first IMU, or setting the tracked pose of the second IMU to the first pose of the second IMU, or both.

In other examples, a third object is configured to couple to at least one of the first object and the second object to achieve a second reproducible reference pose, data is received indicative of the first object being coupled to at least one of the second object in the first reproducible reference pose and the third object in the second reproducible reference pose, and a tracked pose of the second IMU, a third IMU mounted to the third object, or both is reset based on the data. A third object can be configured to couple to at least one of the first object and the second object to achieve a second reproducible reference pose, data can be received indicative of the third object being coupled to the at least one of the first object and the second object in the second reproducible reference pose, and a tracked pose of a third IMU mounted to the third object can be reset based on the data.

In some examples, the second object includes a first portion configured to couple to the first IMU to achieve the first reproducible reference pose and a second portion configured to couple to a second IMU mounted to a third object to achieve a second reproducible reference pose. The inertial tracking system can determine a tracked pose of the second IMU. The intertial tracking system can reset the tracked pose of the first IMU, the tracked pose of the second IMU, or both, when the first IMU is coupled to the first portion of the second object in the first reproducible reference pose and the second IMU is coupled to the second portion of the second object in the second reproducible reference pose. The inertial tracking system can determine that an error associated with the first IMU exceeds a predetermined threshold, and can reset the tracked pose of the first IMU based on the first reproducible reference pose.

In other examples, resetting includes determining the first object and the second object are in the first reproducible reference pose and resetting the tracked pose of the first IMU based on the first reproducible reference pose. Determining the first object and the second object are in the first reproducible reference pose can include determining the second object is kinematically coupled to the first object. Data can be received indicative of the first IMU being kinematically coupled to the second IMU to achieve the reproducible reference pose. A tracked pose of the second IMU can be determined with respect to the first IMU based on the tracked pose of the first IMU, the tracked pose of the second IMU, and the reproducible reference pose.

The techniques, which include both methods and apparatuses, described herein can provide one or more of the following advantages. An inertial tracking system can be used that reduces or eliminates drift that commonly occurs with IMUs by resetting the reference position of the IMUs based on a reproducible reference pose. Reducing or eliminating drift allows the inertial tracking system to more accurately track IMUs. The inertial tracking system can be more cost effective and simpler than other tracking systems. For example, inertial tracking systems do not need to include expensive optical devices or multi-part systems. IMUs (e.g., wireless IMUs) can be easily mounted to a patient's anatomy (e.g., a bone) or surgical instruments (e.g., a haptic device or a probe) without creating line-of-sight barriers. IMUs can be mounted in the same incision made for bone resections, which can eliminate additional incisions required to mount trackers to the patient's anatomy (e.g., bone pins) and can improve patient recovery time. IMUs can be lightweight and small enough to minimize any forces transmitted to the patient compared to other trackers (e.g., compared to optical tracking arrays).

Other aspects and advantages of the present invention will become apparent from the following detailed description, taken in conjunction with the accompanying drawings, illustrating the principles of the invention by way of example only.

BRIEF DESCRIPTION OF THE DRAWINGS

The foregoing and other objects, features, and advantages of the present invention, as well as the invention itself, will be more fully understood from the following description of various embodiments, when read together with the accompanying drawings.

DETAILED DESCRIPTION

Figure 1:
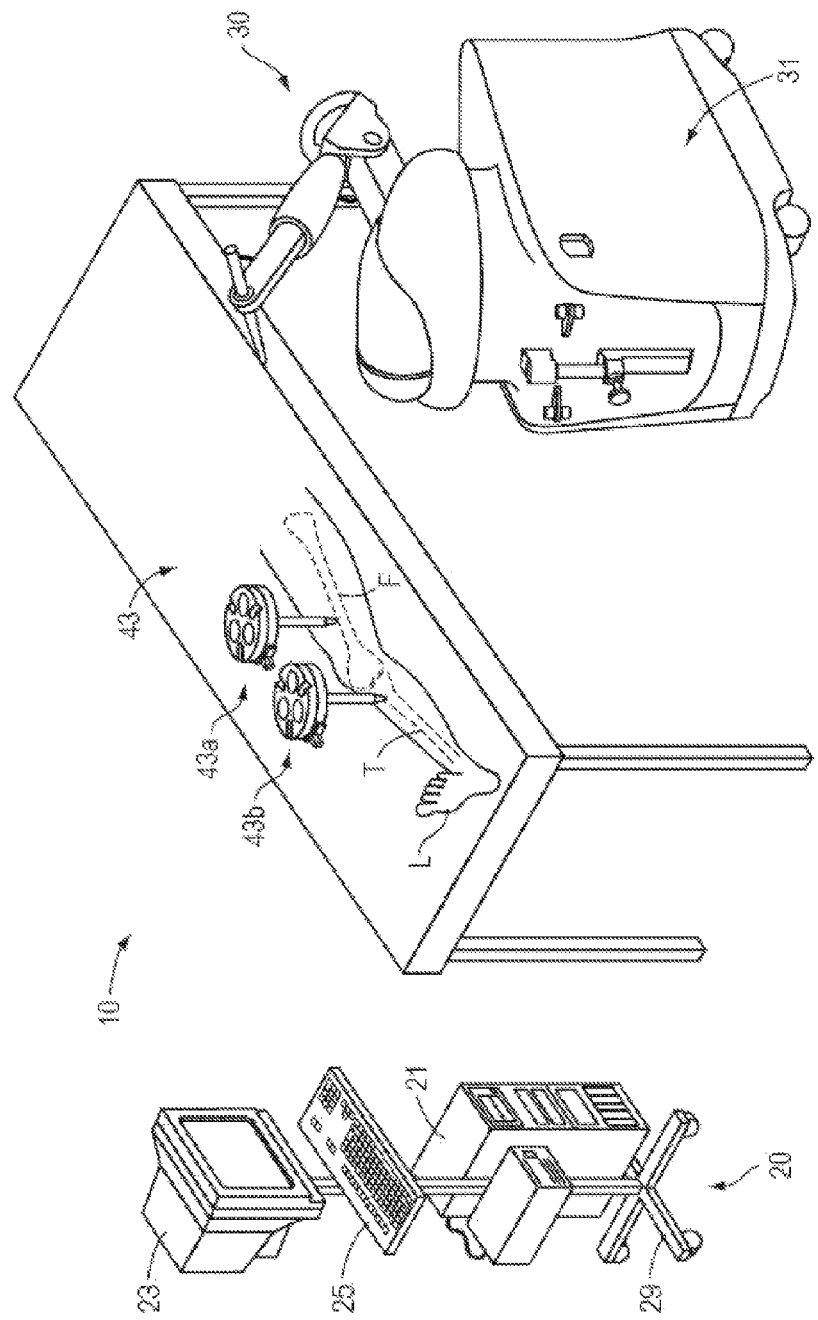
FIG. 1 illustrates an exemplary surgical computer system.

Presently preferred embodiments of the invention are illustrated in the drawings. Although this specification refers primarily to object tracking during image-guided orthopedic surgical procedures involving the knee joint, it should be understood that the subject matter described herein is applicable to other types of navigated surgical procedures, including imageless surgical procedures, as well as to non-surgical applications involving object tracking.

According to the present invention, a reference position for an inertial tracking element or tracker (e.g., for an IMU) can be reset based on a reproducible reference pose to eliminate an error (e.g., drift) associated with the inertial tracker. The reproducible reference pose can be achieved by kinematically coupling the inertial tracker to a second object, such as a second inertial tracker or an untracked coupling element. The inertial tracking system can subsequently track the inertial tracker based on the reset reference position. By utilizing the reproducible reference pose of the present technology, navigated surgical procedures can be accurately and efficiently performed through the manipulation of a surgical tool, both with or without haptic guidance.

FIG. 1 shows an embodiment of an exemplary surgical computer system 10 in which the inertially tracked objects and techniques described herein can be implemented. A similar exemplary system is described in detail, for example, in U.S. Patent Application Publication No. 2006/0142657, published Jun. 29, 2006, which is hereby incorporated by reference herein in its entirety. In a preferred embodiment, the surgical computer system is the the RIO® Robotic Arm Interactive Orthopedic System, manufactured by MAKO Surgical Corp., Fort Lauderdale, Fla. The surgical system 10 includes a computing system 20, a haptic device 30, and a tracking system (which is described in further detail herein). In operation, the surgical system 10 enables comprehensive surgical planning and provides haptic guidance to a surgeon as the surgeon performs a surgical procedure. Although included for completeness in the illustrated embodiment, the haptic device 30 and its associated hardware and software are not necessary to perform the techniques described herein.

The computing system 20 includes hardware and software for operation and control of the surgical system 10. Such hardware and/or software is configured to enable the surgical system 10 to perform the techniques described herein. In FIG. 1, the computing system 20 includes a computer 21, a display device 23, and an input device 25. The computing system 20 may also include a cart 29.

The computer 21 may be any known computing system but is preferably a programmable, processor-based system. For example, the computer 21 may include a microprocessor, a hard drive, random access memory (RAM), read only memory (ROM), input/output (I/O) circuitry, and any other well-known computer component. The computer 21 is preferably adapted for use with various types of storage devices (persistent and removable), such as, for example, a portable drive, magnetic storage (e.g., a floppy disk), solid state storage (e.g., a flash memory card), optical storage (e.g., a compact disc or CD), and/or network/Internet storage. The computer 21 may comprise one or more computers, including, for example, a personal computer (e.g., an IBM-PC compatible computer) or a workstation (e.g., a SUN or Silicon Graphics workstation) operating under a Windows, MS-DOS, UNIX, or other suitable operating system and preferably includes a graphical user interface (GUI).

The display device 23 is a visual interface between the computing system 20 and the user. The display device 23 is connected to the computer 21 and may be any device suitable for displaying text, images, graphics, and/or other visual output. For example, the display device 23 may include a standard display screen (e.g., LCD, CRT, plasma, etc.), a touch screen, a wearable display (e.g., eyewear such as glasses or goggles), a projection display, a head-mounted display, a holographic display, and/or any other visual output device. The display device 23 may be disposed on or near the computer 21 (e.g., on the cart 29 as shown in FIG. 1) or may be remote from the computer 21 (e.g., mounted on a wall of an operating room or other location suitable for viewing by the user). The display device 23 is preferably adjustable so that the user can position/reposition the display device 23 as needed during a surgical procedure. For example, the display device 23 may be disposed on an adjustable arm (not shown) that is connected to the cart 29 or to any other location well-suited for ease of viewing by the user. The display device 23 may be used to display any information useful for a medical procedure, such as, for example, images of anatomy generated from an image data set obtained using conventional imaging techniques, graphical models (e.g., CAD models of implants, instruments, anatomy, etc.), graphical representations of a tracked object (e.g., anatomy, tools, implants, etc.), digital or video images, registration information, calibration information, patient data, user data, measurement data, software menus, selection buttons, status information, and the like.

The input device 25 of the computing system 20 enables the user to communicate with the surgical system 10. The input device 25 is connected to the computer 21 and may include any device enabling a user to provide input to a computer. For example, the input device 25 can be a known input device, such as a keyboard, a mouse, a trackball, a touch screen, a touch pad, voice recognition hardware, dials, switches, buttons, a trackable probe, a foot pedal, a remote control device, a scanner, a camera, a microphone, and/or a joystick.

The computing system 20 is in communication with a computing device 31 of the haptic device 30 and anatomy trackers 43a and 43b, generally 43. The communication interface may be any known interface such as, for example, a wired interface (e.g., serial, USB, Ethernet, CAN bus, and/or other cable communication interface) and/or a wireless interface (e.g., wireless Ethernet, wireless serial, infrared, and/or other wireless communication system) and may include a software interface resident on the computer 21 and/or the computer 31. In some embodiments, computer 21 and 31 are the same computing device.

The surgical system 10 also includes a tracking system, comprising one or more tracking elements (e.g., the anatomy trackers 43). A tracking element is configured to be attached to a tracked object and is registered to the tracked object. Data from the tracking element is used (e.g., by the computer 21 and/or the computer 31) to determine a pose (i.e., position and/or orientation) of the tracked object (i.e., a tracked pose). Tracked objects may include, for example, anatomy, the haptic device 30, surgical tools, and/or other objects of interest. In some embodiments, the tracking system may include a computing device (e.g., a separately located computing device or software and/or hardware that is integrated into the computer 21, the computer 31, and/or the tracking element) that receives data from the tracking element and determines a pose of the tracked object with respect to a coordinate frame of interest, such as a coordinate frame of the tracking system. As is well known, the determined pose can be transformed into other coordinate frames of reference, such as a coordinate frame of a virtual environment of the surgical system 10. Data from the tracking system can be used, for example, to register tracked objects (e.g., to register the patient's bone to an image of the bone) and to track movement of objects during a surgical procedure.

For example, using pose data from the tracking system, the surgical system 10 is able to register (or map or associate) coordinates in one space to those in another to achieve spatial alignment or correspondence (e.g., using a coordinate transformation process as is well known). Objects in physical space may be registered to any suitable coordinate system, such as a coordinate system being used by a process running on the computer 21 and/or the computer 31. For example, utilizing pose data from the tracking system, the surgical system 10 is able to associate the physical anatomy (i.e., physical space) with a representation of the anatomy (such as an image displayed on the display device 23) (i.e., image space). Based on tracked object and registration data, the surgical system 10 may determine, for example, a spatial relationship between the image of the anatomy and the relevant physical anatomy (i.e., between the image space and the physical space). Knowing this relationship, the image of the anatomy (e.g., displayed on the display device 23) can be made to move in correspondence with the movement of the relevant tracked physical anatomy. The surgical system 10 may also determine, for example, a spatial relationship between the relevant physical anatomy and a surgical tool (not shown) so that the computing system 20 can superimpose (and continually update) a virtual representation of the surgical tool on the image of the anatomy, where the relationship between the virtual representation of the surgical tool and the image of the anatomy is substantially identical to the relationship between the physical surgical tool and the actual physical anatomy. Additionally, by tracking not only the surgical tool but also the relevant anatomy, the surgical system can compensate for movement of the relevant anatomy during the surgical procedure (e.g., by adjusting a virtual object that defines an anatomical cutting boundary in response to the detected movement of the physical anatomy).

Registration may include any known registration technique, such as, for example, image-to-image registration (e.g., monomodal registration where images of the same type or modality, such as fluoroscopic images or MR images, are registered and/or multimodal registration where images of different types or modalities, such as MRI and CT, are registered); image-to-physical space registration (e.g., image-to-patient registration where a digital data set of a patient's anatomy obtained by conventional imaging techniques is registered with the patient's actual anatomy); and/or combined image-to-image and image-to-physical-space registration (e.g., registration of preoperative CT and MRI images to an intraoperative scene). One example of a process for registering patient anatomy to an image of the anatomy is described in U.S. Patent Application Pub. No. 2006/0142657, published Jun. 29, 2006, which is hereby incorporated by reference herein in its entirety. The surgical system 10 may also include a coordinate transform process for mapping (or transforming) coordinates in one space to those in another to achieve spatial alignment or correspondence. For example, the surgical system 10 may use the coordinate transform process to map positions of tracked objects (e.g., patient anatomy, etc.) into a coordinate system used by a process running on the computer 31 and/or the computer 21. As is well known, the coordinate transform process may include any suitable transformation technique, such as, for example, rigid-body transformation, non-rigid transformation, affine transformation, and the like.

In addition to registration, the tracking system enables the surgical system 10 to determine (or track), in real-time, poses of tracked objects. According to an embodiment of the present invention, as shown in FIG. 1, the tracking system includes an inertial tracking system that comprises at least one tracking element (or inertial tracker) configured to be disposed on (or incorporated into) a tracked object and a computing device (e.g., the computer 21, the computer 31, and/or a computing device incorporated into the tracking element) for determining a pose (i.e., a tracked pose) of the tracked object. The tracked pose is calculated based on data from the tracking element and a registration between the tracked object and the tracking element. In an exemplary embodiment, the tracking element includes a first inertial tracker (the anatomy tracker 43a) and a second inertial tracker (the anatomy tracker 43b). The anatomy trackers 43a and 43b are configured to be affixed to the tracked objects (i.e., the femur F and the tibia T, respectively) in a secure and stable manner and each includes an IMU having a known geometric relationship to the respective tracked object. The known geometric relationship can be determined, for example, using a conventional registration process. The IMU can be, for example, an Inertia-Link® IMU and Vertical Gyro provided by MicroStrain, Inc., Williston, Vt., a NavChip™ provided by InterSense, Inc., Billerica, Mass., and/or the like. In operation, the IMU measures changes in its acceleration and angular rate over time. This information, combined with an initial (or starting or previous) reference pose of the IMU and the IMU's known geometric relationship to the tracked object, enable the surgical system 10 to calculate a current pose of the tracked object based on the tracked pose of the IMU.

In FIG. 1, the anatomy tracker 43 is disposed on a relevant portion of a patient's anatomy (such as a bone). The anatomy tracker 43 includes a fixation device for attachment to the anatomy. The fixation device may be, for example, a bone pin, surgical staple, screw, clamp, wearable device, intramedullary rod, or the like. In some embodiments, the anatomy tracker 43 is configured for use during knee replacement surgery to track the femur F and the tibia T of the patient. In the embodiment of FIG. 1, the anatomy tracker 43 includes a first tracker 43a adapted to be disposed on the femur F and a second tracker 43b adapted to be disposed on the tibia T. When installed on the patient and registered to the respective portion of the anatomy, the first and second trackers 43a and 43b enable the tracking system to determine tracked poses of the femur F and the tibia T in real-time. While embodiments have described the tracking system as being an inertial tracking system, the tracking system may additionally include any other type of tracking system (e.g., optical, mechanical, electromagnetic, fiber optic, and the like).

Figure 2:
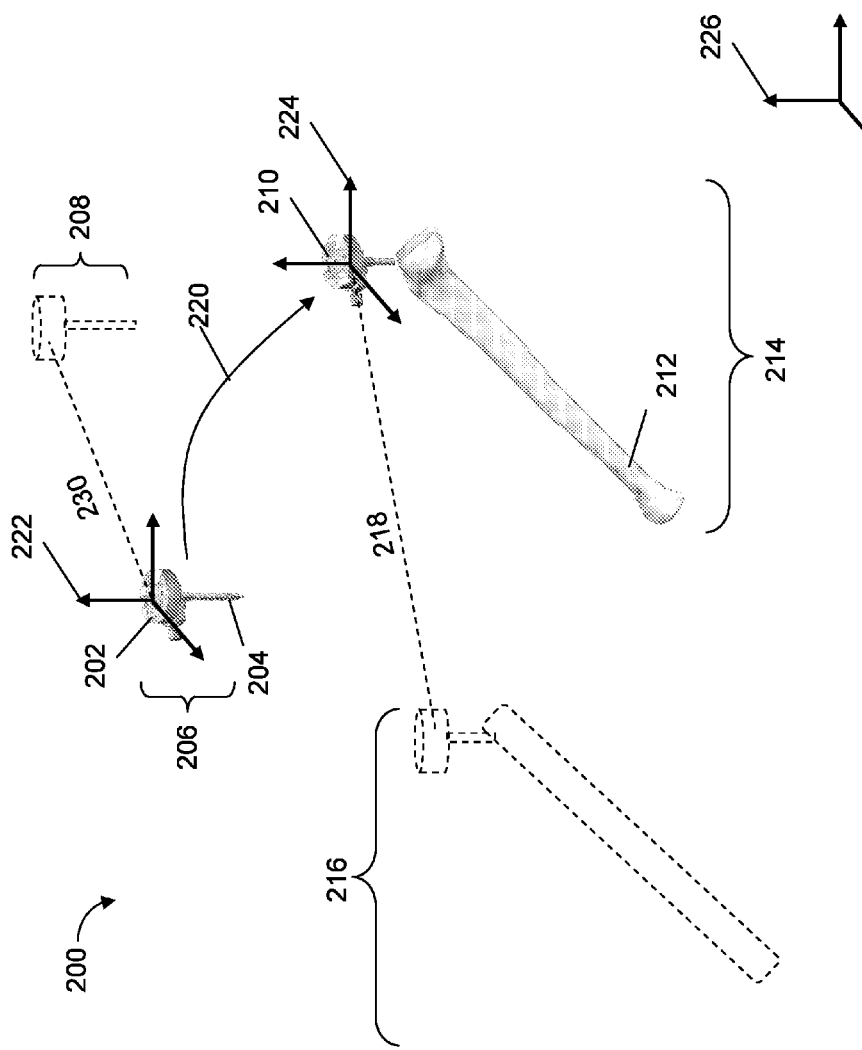
FIG. 2 illustrates an exemplary diagram of poses of inertially tracked objects and drifts associated with the inertially tracked objects.

FIG. 2 illustrates an exemplary diagram 200 of poses of inertially tracked objects and drifts associated with the inertially tracked objects. The diagram 200 includes a first inertial tracker, a first IMU 202, mounted and registered to a first object, a probe 204 (an inertially tracked probe). The actual IMU pose 206 is the actual pose of the first IMU 202 and the probe 204 in three-dimensional physical space (e.g., in a preoperative/intraoperative scene, such as an operating room). The tracked IMU pose 208 is the corresponding tracked pose of the first IMU 202 (and the tracked pose of the probe 204). For purposes of illustration, the tracked IMU pose 208 is shown in the same coordinate frame of reference as the actual IMU pose 206 but could be transformed into any coordinate frame of interest, such as, for example, three-dimensional image space, as is well known. As a result of the accumulated error of the IMU 202, there is a drift 230 between the actual IMU pose 206 and the tracked IMU pose 208. The diagram 200 includes a second inertial tracker, a second IMU 210, mounted and registered to a second object, a bone 212. The actual IMU pose 214 is the actual pose of the second IMU 210 in the three-dimensional physical space, and the tracked IMU pose 216 is the corresponding tracked pose of the second IMU 210 (and the tracked pose of the bone 212). There is a drift 218 between the actual IMU pose 214 and the tracked IMU pose 216.

Figure 3:
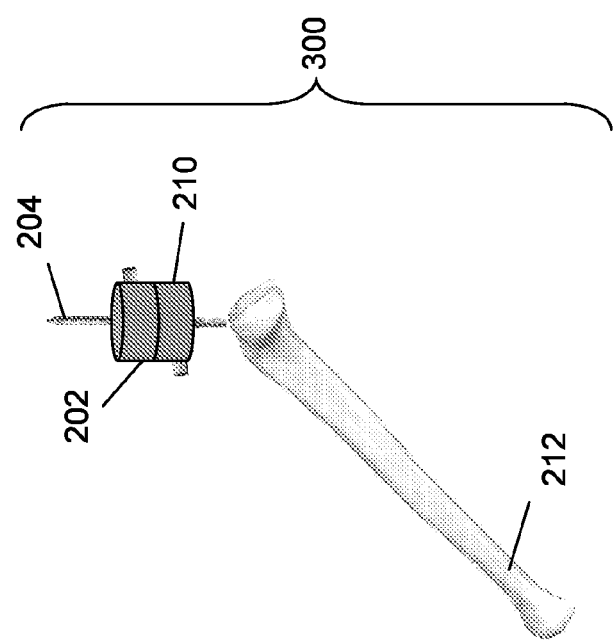
FIG. 3 illustrates an exemplary diagram of a reproducible reference pose for two inertially tracked objects.

According to an embodiment of the present invention, tracking error caused by drift (e.g., the drift 230 or the drift 218) can be mitigated by using a reproducible reference pose. FIG. 3 illustrates an exemplary diagram of a reproducible reference pose 300 for two inertially tracked objects. In the reproducible reference pose, the inertially tracked objects have a known geometric relationship relative to one another (determined, for example, using registration and/or calibration processes). The reproducible reference pose can be established between the tracked objects such that the tracked objects can be repeatedly and accurately placed into the reproducible reference pose to reset a tracking calculation between the objects. For example, prior to tracking the relative position of the tracked objects, the tracked objects can be temporarily coupled together in the reproducible reference pose to establish an initial (or starting) reference pose for the tracked objects. The tracked objects can then be decoupled and tracked by the inertial tracking system. When the drift associated with the inertial tracker of one (or both) tracked objects becomes too large, the tracked objects can be placed back into the reproducible reference pose to reset (i.e., unbias or "zero") the pose of one inertial tracker relative to the other to thereby eliminate the drift error. The reproducible reference pose can be achieved, for example, by temporarily kinematically coupling the inertial trackers of the tracked objects together. The inertial tracking system can subsequently track the inertial trackers based on this reset reference position. In the embodiment of FIG. 3, the reproducible reference pose 300 includes the first IMU 202 removably coupled to the second IMU 210. The first IMU 202 (and the probe 204) and the second IMU 210 (and the bone 212) can be placed into the reproducible reference pose as indicated by arrow 220 in FIG. 2. The first IMU 202 and the second IMU 210 can include, for example, kinematic couplings as described with reference to FIGS. 5A-5C below. As described with reference to FIG. 2, the first IMU 202 is mounted and registered to the probe 204, and the second IMU 206 is mounted and registered to the bone 212. Because the coupling between the first and second IMUs 202, 210 is kinematic, the exact pose of the first IMU 202 with respect to the second IMU 210 (or vice versa) is known (e.g., via a predetermined transformation) when the IMUs 202, 210 are placed into the reproducible reference pose. Similarly, from the registration process, a predetermined transformation is known between the first IMU 202 and the probe 204 and between the second IMU 210 and the bone 212 such that the exact pose of the probe 204 with respect to the bone 212 can be determined.

The predetermined transformations can be determined using conventional calibration, registration, and/or coordinate transformation processes. For example, the first IMU 202 includes a first IMU coordinate frame 222, and the second IMU 210 includes a second IMU coordinate frame 224 (e.g., the coordinate frames of inertial sensors of the IMUs). The diagram 200 includes a reference frame 226, which can be any coordinate frame of interest, such as the coordinate system of the inertial tracking system, the coordinate system of the image space, or another coordinate system of interest. As is well known, transformations can be calculated between the objects and the IMUs (e.g., between the bone 212 and the second IMU 210 as described below with reference to FIG. 4) such that the coordinate frame of the object can be mapped to the coordinate frame of the IMU (or vice versa), which can then be transformed into the reference frame 226.

Although the IMUs 202, 210 are described in connection with a probe and a bone, in other embodiments, IMUs can be mounted to other objects (e.g., other portions of anatomy, a surgical tool, a cutting jig, an operating table, a floor, the haptic device 30, etc.). Additionally, the length of the drifts 230 and 218 can be larger or smaller. For example, the drift can become larger over time (e.g., the drift can effectively be zero when the inertial tracking system begins tracking the IMUs and increase over time). The tracked IMU poses 208 and 216 are shown as exemplary three dimensional shifts from the actual IMU poses 206 and 214. The tracked IMU poses 208 and 216 can drift in any position and/or orientation from the actual IMU poses 206 and 214 (e.g., the tracked IMU pose 208 can be above the actual IMU pose 206, below the actual IMU pose 206, etc.).

In one embodiment, multiple IMUs can be affixed to a single object and used to track the object. For example, two or more IMUs can be affixed to a bone or other tracked object. One advantage of using multiple IMUs to track a single object is that pose data from the multiple IMUs can be averaged to minimize drift error. In one embodiment, there are multiple IMUs on a single object (e.g., a bone) but only one coupling (e.g., a kinematic coupling). The coupling can be affixed to one of the IMUs or mounted separately to the object. A relationship between the coordinate systems of the multiple IMUs and/or between the IMUs and the coupling can be established via registration. To reset all of the IMUs, another tracked object (e.g., a tracked probe) can be coupled to the coupling as described herein. In particular, once the pose of any IMU on the object is registered to the pose of the coupling (or to another IMU that is registered to the coupling), resetting of that IMU can be accomplished by coupling the tracked object to the coupling, provided the IMUs and the coupling are affixed to the object in a stable manner and do not move relative to each other or the object. Advantageously, in this embodiment, the pose data from the multiple IMUs can be averaged to minimize drift.

According to an embodiment, multiple IMUs (e.g., two IMUs) can be used to track multiple objects (e.g., two objects) where one IMU is affixed to each object. For example, as described above in connection with FIGS. 2 and 3, both the IMU 202 and the IMU 210 can be used to simultaneously track the probe 204 and the bone 212, respectively. The IMUs 202, 210 can be coupled together to create the reproducible reference pose 300, and the poses for both the IMU 202 and the IMU 210 can be reset based on the reproducible reference pose. Using two IMUs to track two objects (where an IMU is mounted to each object) and resetting the reference poses of the IMUs when the two objects are placed in a reproducible reference pose is further described with reference to FIG. 6.

In another embodiment, one IMU can be used to track a first object while a second object is untracked. The second object may be, for example, a bone that is fixed in place thereby eliminating the need to track the bone. In this embodiment, the reproducible reference pose is similar to the reproducible reference pose 300 of FIG. 3 except the IMU 210 is replaced with an untracked coupling element (e.g., a kinematic coupling) that is mounted to the bone 212 and that does not include an IMU. Alternatively, the IMU 210 can be temporarily (or permanently) deactivated. To reset the IMU 202, the IMU 202 (attached to the probe 204) and the untracked coupling element (attached to the bone 212) are placed into a reproducible reference pose (e.g., the reproducible reference pose 300) as described above in connection with FIG. 3. Using an IMU to track one object and resetting the IMU's reference pose when the first object is coupled to a second untracked object in a reproducible reference pose is further described with reference to FIG. 4.

Figure 4:
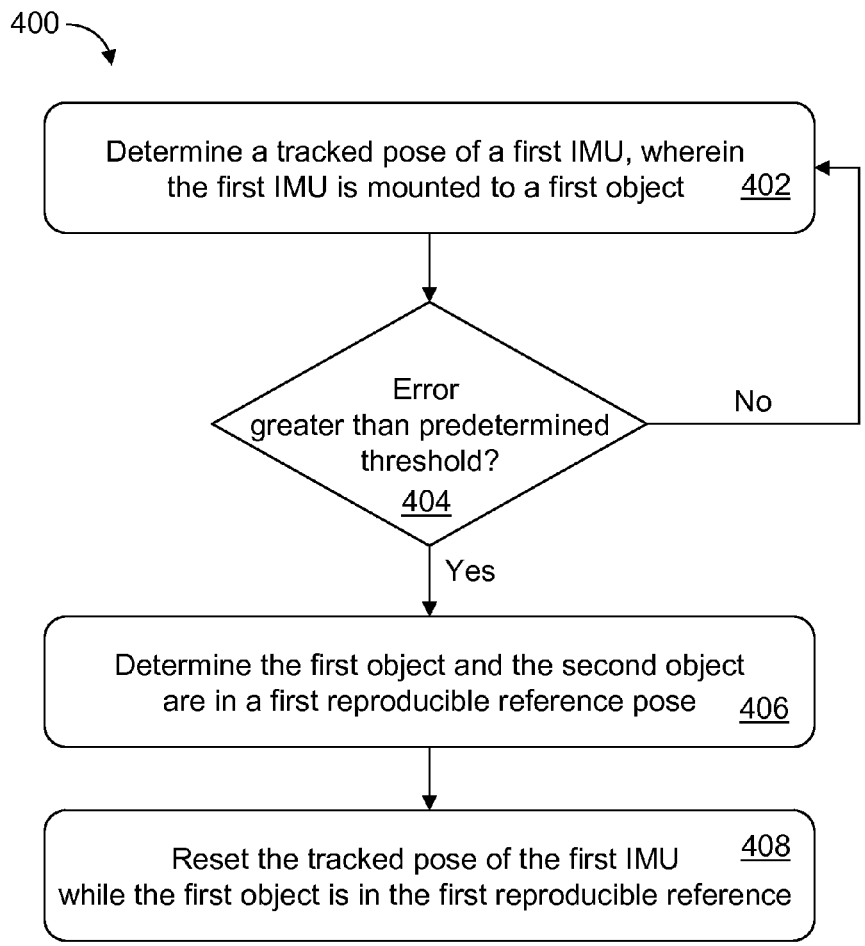
FIG. 4 illustrates an exemplary computer implemented method for resetting an inertial tracking element.

FIG. 4 illustrates an exemplary computer implemented method 400 for resetting an inertial tracking element (e.g., an IMU). This embodiment describes using one inertial tracker to track a first object (e.g., a surgical instrument comprising an IMU), where a first IMU is mounted to a first object, while a second object is untracked. Preferably, prior to step 402, the first and second objects are placed in a first reproducible reference pose to establish an initial (or starting) reference pose of the first IMU. At step 402, the inertial tracking system determines a tracked pose of the first IMU. At step 404, the inertial tracking system determines whether an error associated with the first IMU exceeds a predetermined threshold. For instance, in one embodiment, for surgical navigation, the predetermined threshold can be approximately 0.3 mm and 0.3 degrees. If the error does not exceed the predetermined threshold, the method 400 proceeds back to step 402. If the error exceeds the predetermined threshold, the method 400 proceeds to step 406. At step 406, the inertial tracking system determines the first object and the second object are in the first reproducible reference pose. At step 408, the inertial tracking system resets the tracked pose of the first IMU while the first object is in the first reproducible reference pose with the second object.

Referring to step 402 and FIG. 2, for example, the inertial tracking system (e.g., the inertial tracking system described above with reference to FIG. 1) determines the tracked IMU pose 208 of the first IMU 202. The first IMU 202 can calculate various measurements indicative of the pose of the first IMU 202 (e.g., angular rate, angular position, Euler angles, rotation matrices, linear acceleration, and linear velocity). The measurements can be used (e.g., by the first IMU 202, the inertial tracking system, etc.) to estimate a six degree of freedom (6 DOF) pose of the first IMU 202. For example, linear acceleration vectors and angular rate vectors can be integrated to estimate the pose of the first IMU 202.

In some embodiments, IMU measurements are transformed to a reference coordinate frame (e.g., the inertial tracking system's coordinate frame). For example, the inertial tracking system can transform the first IMU 202 measurements, which are calculated in the first IMU coordinate frame 222, to the reference frame 226. In some examples, the rotation between the reference frame 226 and the first IMU coordinate frame 222 can be calculated based on infinitesimal rotation matrices (e.g., differential rotations) and/or integrated using known differential equations.

When an IMU is attached to an object (e.g., a rigid body), the estimated 6 DOF pose of the IMU can be used to calculate a 6 DOF pose of the object. Referring to FIG. 2, the first IMU 202 is mounted to the probe 204. A transformation between the pose of the first IMU 202 and the pose of the probe 204 can be determined, thereby allowing the inertial tracking system to calculate a tracked pose of the probe 204 based on the tracked pose of the first IMU 202 (e.g., based on a known geometry between the IMU 202 and the probe 204 determined using conventional calibration and/or registration processes). For example, a predetermined transformation can be established between the origin of the IMU 202 and the tip of the probe 204. Advantageously, the inertial tracking system can determine the tracked IMU pose 208 and use the predetermined transformation to determine the tracked pose of the probe 204.

Some objects may not have a known geometry with respect to the IMU. For example, the second IMU 210 can be intraoperatively mounted to the patient's bone 212, such that the geometric relationship between the second IMU 210 and the bone 212 is unknown. When the second IMU 210 is mounted to the bone 212, the transformation between the second IMU 210 and the bone 212 can be determined by registering the bone 212. For example, the IMU 202 attached to the probe 204 (e.g., a sharp probe) can be used to collect positions (points) on the surface of the bone 212. The inertial tracking system can use the collected positions to fit the bone 212 to a preoperatively obtained three dimensional model of the bone (e.g., obtained from a CT scan, MRI scan, etc.). For example, the collected points can be fit to the three dimensional model of the bone 212 to register the bone 212 (e.g., in a least-squares manner). In some embodiments, the first IMU 202 and the second IMU 210 can be placed into a reproducible reference pose (e.g., as described with reference to FIG. 3) to reset a reference position (a starting position) for the first IMU 202 and/or the second IMU 210 before collecting the positions on the bone 212. In some examples, other tools and/or methods can be used to calculate the transformation between the second IMU 210 and the bone 212. For example, a multi-degree of freedom robotic arm can be used to collect positions on the surface of the bone 212. This is further described with reference to FIGS. 7-8. As described with reference to FIG. 1, registration may include any known registration technique, such as, for example, image-to-image registration, image-to-physical space registration, and/or combined image-to-image and image-to-physical-space registration.

Referring to step 404, over time an IMU accumulates error or drift, resulting in a disassociation between the actual IMU pose and the tracked IMU pose (e.g., the drift 230 between the actual IMU pose 206 and the tracked IMU pose 208). The inertial tracking system can be configured to estimate when the error associated with an IMU (the drift) exceeds a certain threshold, requiring the reference pose of the IMU to be reset. For example, the inertial tracking system can be configured to alert a user every ten minutes, fifteen minutes, or other time interval that the drift has grown too large (e.g., based on a theoretical rate of drift, the elapsed amount of time since the last reset, etc.). Another way to trigger when to reset the reference pose is to use a checkpoint (e.g., a mechanical divot) as described, for example, in U.S. Patent Pub. No. US 2008/0004633, published Jan. 3, 2008, and hereby incorporated by reference herein in its entirety. For example, a checkpoint can be affixed to a bone and then coupled with an IMU to confirm that the distance between the IMU origin and the checkpoint has not shifted.

Although some embodiments of the present application describe the use of a predetermined threshold for determining when to reset an IMU, an IMU can be reset at any time by placing the IMU into the reproducible reference pose whether or not the error is greater or less than a predetermined threshold. For example, method 400 can omit step 404 and proceed directly to step 406 whenever the surgeon desires, such as two or three times during a surgical procedure, after an elapsed period of time (e.g., ten minutes), and/or whenever the surgeon thinks a reset may be appropriate. Similarly, method 600 (shown in FIG. 6) can omit step 606 and proceed directly to the step 608.

Referring to step 406, the inertial tracking system determines the first and second objects are in the first reproducible reference pose (e.g., a reproducible reference pose like that shown in FIG. 3). For example, assume the untracked second object is a bone (e.g., the bone 212) that is fixed in place and includes an untracked coupling element mounted to the bone (e.g., a coupling element similar to that shown as IMU 210 in FIGS. 2 and 3 except the untracked coupling element does not include an IMU or the IMU has been deactivated). The first object, for example, a surgical instrument (e.g., the first IMU 202 and probe 204), can be tracked with respect to the untracked bone using only one IMU (e.g., the first IMU 202). The reproducible reference pose can be achieved by coupling the first IMU to the untracked coupling element mounted to the bone.

Figure 5A:
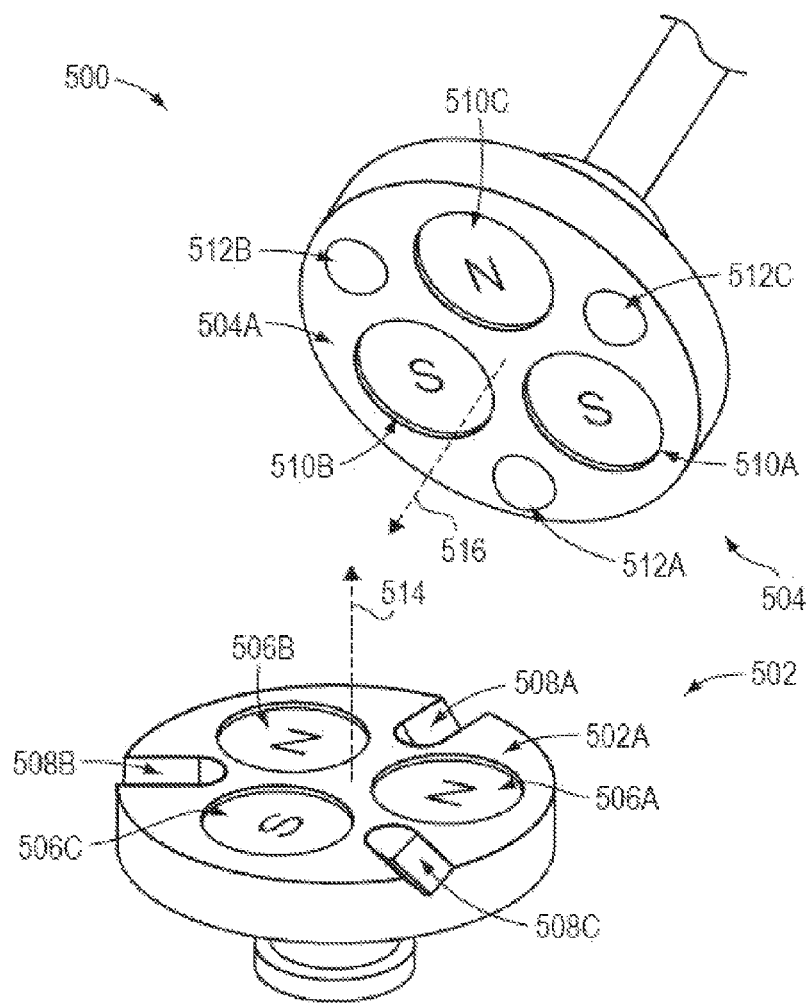
FIGS. 5A-5C illustrate an exemplary embodiment of a kinematic coupling for establishing a reproducible reference pose.
Figure 5B:
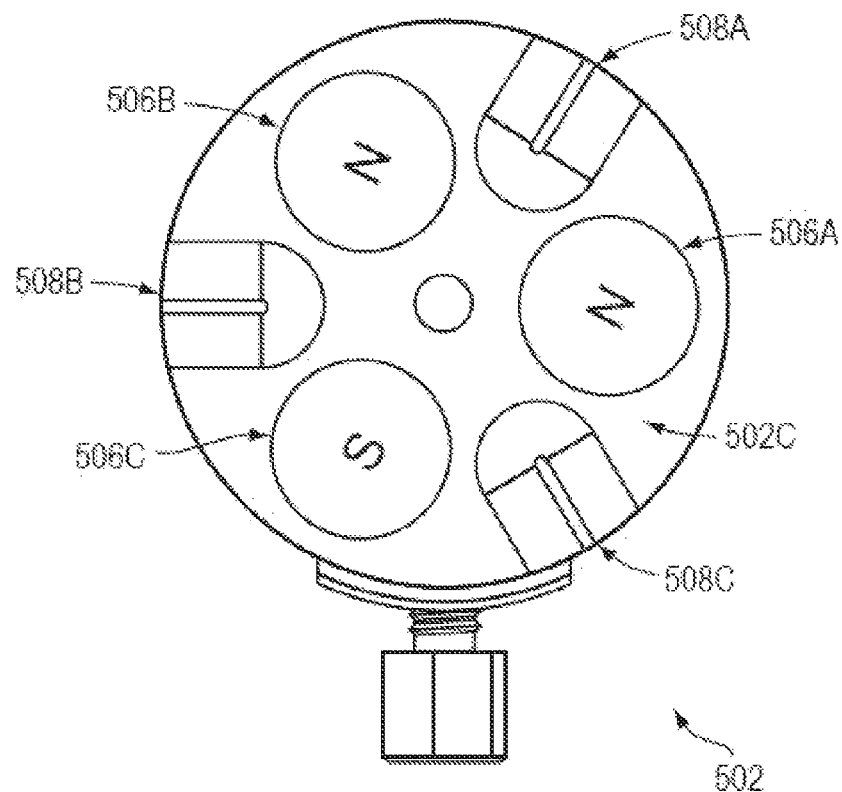
Figure 5C:
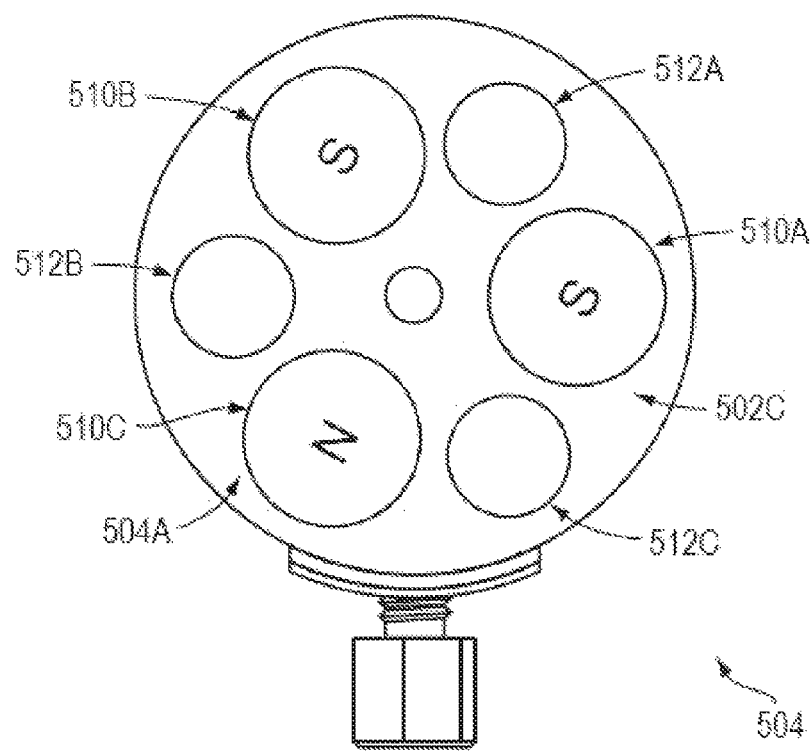

The inertial tracking system can determine the first object and the second object are in the first reproducible reference pose based on a coupling between the first object and a second object. For example, the first IMU can include a first coupling configured to couple to a second coupling mounted to the second object to achieve the first reproducible reference pose. In some embodiments, the first IMU is configured to kinematically couple to the first object. FIGS. 5A-5C illustrate an exemplary embodiment of a kinematic coupling 500 for establishing a reproducible reference pose. Further, for example, U.S. patent application Ser. No. 12/479,510 (U.S. Pub. No. 2009/0306499), which is hereby incorporated by reference herein in its entirety, describes a kinematic coupling for a self-detecting kinematic clamp assembly. FIGS. 5A-5C illustrate different views of the kinematic coupling 500 and thus the following description is generally applicable and refers to any of the views. While FIGS. 5A-5C show an embodiment of a kinematic coupling, one skilled in the art can appreciate that the kinematic coupling can be any type of repeatable kinematic mount.

The kinematic coupling 500 includes a first coupling 502 and a second coupling 504 that are adapted to be repeatedly, accurately, and removably, coupled together to achieve a reproducible reference pose, such as the reproducible reference pose 300 shown in FIG. 3. In some embodiments, the first and/or second couplings 502, 504 can be disposed on an inertial tracker (e.g., on an IMU) and/or on an element or part (or connection portion) that does not include an inertial tracker. In some embodiments, the first and/or second couplings 502, 504 can include an IMU (e.g., the couplings can comprise an inertial tracker). The first and/or second couplings 502, 504 can be adapted to connect to an object. For example, the first and/or second couplings 502, 504 can be removably secured to an object (e.g., a bone) or permanently secured to an object (e.g., a surgical instrument). The first and second couplings 502, 504 are preferably configured to be removably engaged together in a specific geometric configuration and to resist engagement in other geometric configurations. For example, in one embodiment, the first coupling 502 comprises magnets 506A, 506B and 506C, collectively magnets 506, and grooves (e.g., v-grooves) 508A, 508B and 508C, collectively grooves 508. The second coupling 504 comprises magnets 510A, 510B and 510C, collectively magnets 510, and balls 512A, 512B and 512C, collectively balls 512. In some embodiments, the balls 512 are steel balls.

The magnets 506 of the first coupling 502 and the magnets 510 of the second coupling 504 are positioned so that when the engagement surface 502A of the first coupling 502 is brought into close proximity with the engagement surface 504A of the second coupling 504, each of the magnets 506 is aligned over a corresponding magnet 510 (e.g., the magnet 506A is substantially aligned with the magnet 510A, the magnet 506B is substantially aligned with the magnet 510B, and the magnet 506C is substantially aligned with the magnet 510C). Preferably, the magnets 506, 510 are oriented to generate an attraction force only when the first and second couplings 502, 504 are arranged in a particular relative geometric configuration. For example, the magnets 506, 510 are oriented such that the poles of the magnets 506 located on the engagement surface 502A have the opposite polarity of the poles of the corresponding magnets 510 located on the engagement surface 504A so that when the magnets 506, 510 are properly aligned and placed in close proximity (e.g., the north pole (N) of the magnet 506A is placed in close proximity to the south pole (S) of the magnet 510A, the north pole (N) of the magnet 506B is placed in close proximity to the south pole (S) of the magnet 510B, and the south pole (S) of the magnet 506C is placed in close proximity to the north pole (N) of the magnet 510C) the opposite poles attract and the first coupling 502 becomes kinematically assembled (e.g., repeatably, accurately, and removably connected) to the second coupling 504. The magnets 506 and 510 enable quick assembly and disassembly of the first coupling 502 from the second coupling 504 and also prevent assembly of the kinematic coupling 500 in an incorrect configuration. As can be seen in FIG. 5A, the magnets 506, 510 are arranged such that the magnets 506, 510 would resist or oppose misalignment of the couplings 502, 504. For example, if the second coupling 504 is rotated such that the magnet 510A is aligned over the magnet 506C, the south poles (S) of the magnets 510A and 506C would repel one another thereby causing the second coupling 504 to repel or oppose the first coupling 502. Advantageously, the magnets 510 and 506 can be configured such that each of the magnets 510 is attracted to a corresponding magnet 506 only when the first coupling 502 and the second coupling 504 are in the proper relative orientation.

The grooves 508 and the balls 512 are arranged symmetrically around a central axis 514, 516 of each coupling 502, 504. When the engagement surface 502A of the first coupling 502 is brought into close proximity to the engagement surface 504A of the second coupling 504 in the proper geometric configuration, the balls 512 are oriented over the grooves 508 so that each ball 512 sits in a corresponding groove 508 (e.g., the ball 512A sits in the groove 508A). Advantageously, in some embodiments the alignment of the balls 512 and the grooves 508 ensures that each time the second coupling 504 is disconnected, and then re-connected to the first coupling 502, the second coupling 504 returns to exactly the same position. Thus, a specific assembly configuration of the first coupling 502 to the second coupling 504 can be easily preserved regardless of the number of times the second coupling 504 is connected to or removed from the first coupling 502. In one embodiment, the balls 512 should be of sufficient size so that when the first coupling 502 is kinematically assembled to the second coupling 504, there is a slight gap between the engagement surface 502A of the first coupling 502 and the engagement surface 504A of the second coupling 504.

FIGS. 5A-5C show three balls 512 and three corresponding grooves 508, which result in a true kinematic coupling because the six degrees of freedom of the kinematic coupling 500 are constrained by six points of contact. However, other configurations can also be used to removably connect the first coupling 502 to the second coupling 504 without departing from the principles described herein. For example, the grooves 508 can be located on the second coupling 504 and the balls 512 can be located on the first coupling 502. In alternative embodiments, features other than balls and grooves can be employed, as described, for example, in U.S. patent application Ser. No. 12/644,964, filed Dec. 22, 2009, and incorporated by reference herein in its entirety. In some examples, the second coupling 504 can be removably connected to the first coupling 502 using a Maxwell Mount, a Kelvin Mount, a Canoe Ball/Vee Groove Mount, a Three Tooth Coupling, a semi-kinematic mount, or any other type of removable, repeatable connection. In some embodiments, if departing from a true kinematic coupling, care should be taken to not over-constrain the design, which can result in increased wear and tear on the components (e.g., the grooves 508 of the first coupling 502 and the balls 512 of the second coupling 504). Additionally, the kinematic coupling 500 can include any number of magnets or no magnets.

Advantageously, because the kinematic coupling 500 allows the second coupling 504 to be repeatedly and accurately attached to and removed from the first coupling 502, the first coupling 502 and the second coupling 504 can be repeatedly connected to achieve the reproducible reference pose. For example, the IMU 202 can be configured to include the first coupling 502, and a bone can include a connector configured to include the second coupling 504 (the connector need not include an IMU). The IMU 202 can be kinematically coupled to the connector to achieve a reproducible reference pose similar to, for example, the reference pose 300 in FIG. 3.

The kinematic coupling 500 can include a detection mechanism. The detection mechanism can include a state indicator that indicates a coupling of the first and second couplings 502, 504 of the kinematic coupling 500 based on the detection mechanism. In some embodiments, the detection mechanism can include a circuit configured to monitor contact points between the grooves 508 and balls 512. In some embodiments, the detection mechanism can include load sensors (e.g., on the sides of the grooves 508) configured to measure load from the balls 512. The inertial tracking system can use the value of the state indicator to determine when the first and second objects (e.g., when kinematic couplings mounted to the first and second objects) are properly coupled to achieve the reproducible reference pose.

Referring to step 408, the inertial tracking system resets the tracked pose of the first IMU while the first object is in the first reproducible reference pose with the second object. In one embodiment, an optical or magnetic proximity sensor, or electrical circuit, can be used to automatically reset the inertial sensor of the first IMU once the two mating kinematic couplings are connected. Alternatively, the surgical system 10 can include a manual reset switch or software button activated by the surgeon. When the kinematic couplings are connected, the reference pose of the first IMU is reset (e.g., the tracked IMU pose is set to equal the reference pose), such that the pose of the first IMU relative to the second object can be determined based on known transformations between the first IMU and the untracked coupling element and between the untracked coupling element the second object (e.g., the bone 212). For example, a predetermined transformation can be calculated from the coordinate system for an IMU on a surgical instrument to a coordinate system of the bone. The exact pose of the IMU to the bone is known when the surgical instrument and the bone are placed in the reproducible reference pose (e.g., via kinematic couplings on the surgical instrument and the bone). For example, the transformation from the coordinate system of the IMU to the coordinate system of the untracked coupling element mounted to the bone can be predetermined. Further, a transformation from the coordinate system of the untracked coupling element to the bone can be determined via, for example, a registration process. Once the first IMU is reset, each new pose (tracked IMU pose) can be calculated as an offset from the IMU reference, or starting, position. Throughout a surgical procedure, the first and second objects can be reconnected in the first reproducible reference pose as often as necessary (e.g., based on step 404) to reset the first IMU reference position (and to consequently zero-out the drift).

Figure 6:
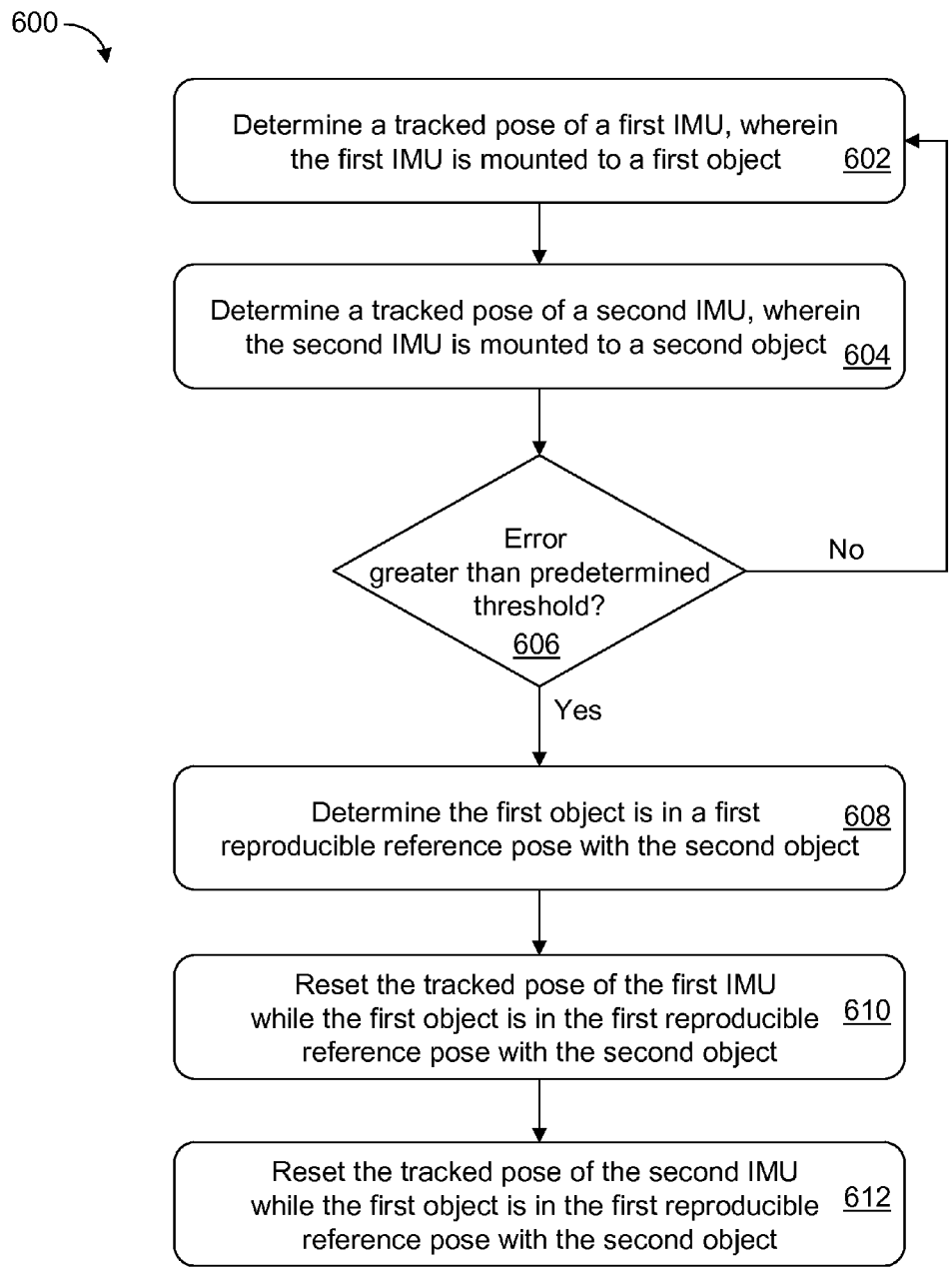
FIG. 6 illustrates an exemplary computer implemented method for resetting the reference pose for multiple inertially tracked objects.

While method 400 of FIG. 4 describes using one inertial tracker to track an object (e.g., a surgical instrument comprising an IMU), more than one inertial tracker can be used to track multiple objects. FIG. 6 illustrates an exemplary computer implemented method 600 for resetting the reference position of multiple tracked objects, where a first IMU is mounted to a first object and a second IMU is mounted to a second object. Preferably, prior to step 602, the first and second objects are placed in a first reproducible reference pose to establish an initial (or starting) reference pose of the first and second IMUs. At step 602, the inertial tracking system determines a tracked pose of the first IMU. At step 604, the inertial tracking system determines a tracked pose of the second IMU. At step 606, the inertial tracking system determines whether an error associated with the first IMU, the second IMU, or both exceeds a predetermined threshold. If neither error is greater than the predetermined threshold, the method 600 proceeds back to step 602. If one or more of the errors is greater than the predetermined threshold, the method 600 proceeds to step 608. At step 608, the inertial tracking system determines the first object is in a first reproducible reference pose with the second object. At step 610, the inertial tracking system resets the tracked pose of the first IMU while the first object is in the first reproducible reference pose with the second object. At step 612, the inertial tracking system resets the tracked pose of the second IMU while the first object is in the first reproducible reference pose with the second object. Although some embodiments of the present application describe the use of a predetermined threshold for determining when to reset an IMU, an IMU can be reset at any time by placing the IMU into the reproducible reference pose regardless of whether the error is greater than or less than a predetermined threshold.

Referring to steps 602-604 and FIG. 2, the inertial tracking system determines the tracked IMU pose 208 of the first IMU 202 and the tracked IMU pose 216 of the second IMU 210. Referring to step 606, the inertial tracking system determines that an error associated with the first IMU 202 and/or the second IMU 210 is greater than a predetermined threshold. The error is indicative of a discrepancy between the tracked IMU pose 208 and the actual IMU pose 206 (drift 230) and/or a discrepancy between the tracked IMU pose 216 and the actual IMU pose 214 (drift 218).

Referring to step 608, the first IMU can include a first kinematic coupling and the second IMU can include a second kinematic coupling. For example, the first IMU 202 can include the first coupling 502 of the kinematic coupling 500 and the second IMU 210 can include the second coupling 504 of the kinematic coupling 500. The inertial tracking system can receive data indicative of the first IMU 202 being kinematically coupled to the second IMU 210 to achieve the reproducible reference pose 300 of FIG. 3. In some embodiments, the tracked IMU pose 208, the tracked IMU pose 216, or both, are reset when the kinematic coupling on the first IMU 202 is kinematically coupled to the kinematic coupling on the second IMU 210. Referring to steps 610 and 612, the inertial tracking system resets the tracked IMU pose 208 of the first IMU 202 and the tracked IMU pose 216 of the second IMU 210 based on the reproducible reference pose 300 (e.g., resets a reference pose for the IMUs). In some examples, the inertial tracking system can reset just one of the tracked IMU poses (e.g., just the tracked IMU pose 208 or the tracked IMU pose 216). For example, if only the error associated with the first IMU is over the predetermined threshold, the inertial tracking system can just reset the tracked pose of the first IMU.

The inertial tracking system can determine a tracked pose of the second IMU with respect to the first IMU based on the tracked pose of the first IMU, the tracked pose of the second IMU, and the first reproducible reference pose. The first reproducible reference pose can include a predetermined transformation indicative of a first pose of the second IMU with respect to a first pose of the first IMU. For example, the reproducible reference pose 300 can include a predetermined transformation indicative of a first pose (a reference pose) of the second IMU with respect to a first pose of the first IMU. The inertial tracking system can calculate the exact pose (e.g., position and orientation) of the first IMU 202 and the second IMU 210 based on the predetermined transformation (e.g., when the first IMU 202 and the second IMU 210 are in the reproducible reference pose 300). The inertial tracking system can set the tracked IMU pose 208 of the first IMU 202 to the first pose of the first IMU, and can set the tracked IMU pose 216 of the second IMU 210 to the first pose of the second IMU. The inertial tracking system can track (e.g., determine tracked poses) for the first IMU 202 and the second IMU 210 after the first IMU 202 and the second IMU 210 leave the reproducible reference pose 300. Advantageously, the inertial tracking system can calculate (in real time) the pose of the first and second IMUs with respect to each other based on the predetermined transformation and/or the tracked poses of the IMUs.

Figure 7:
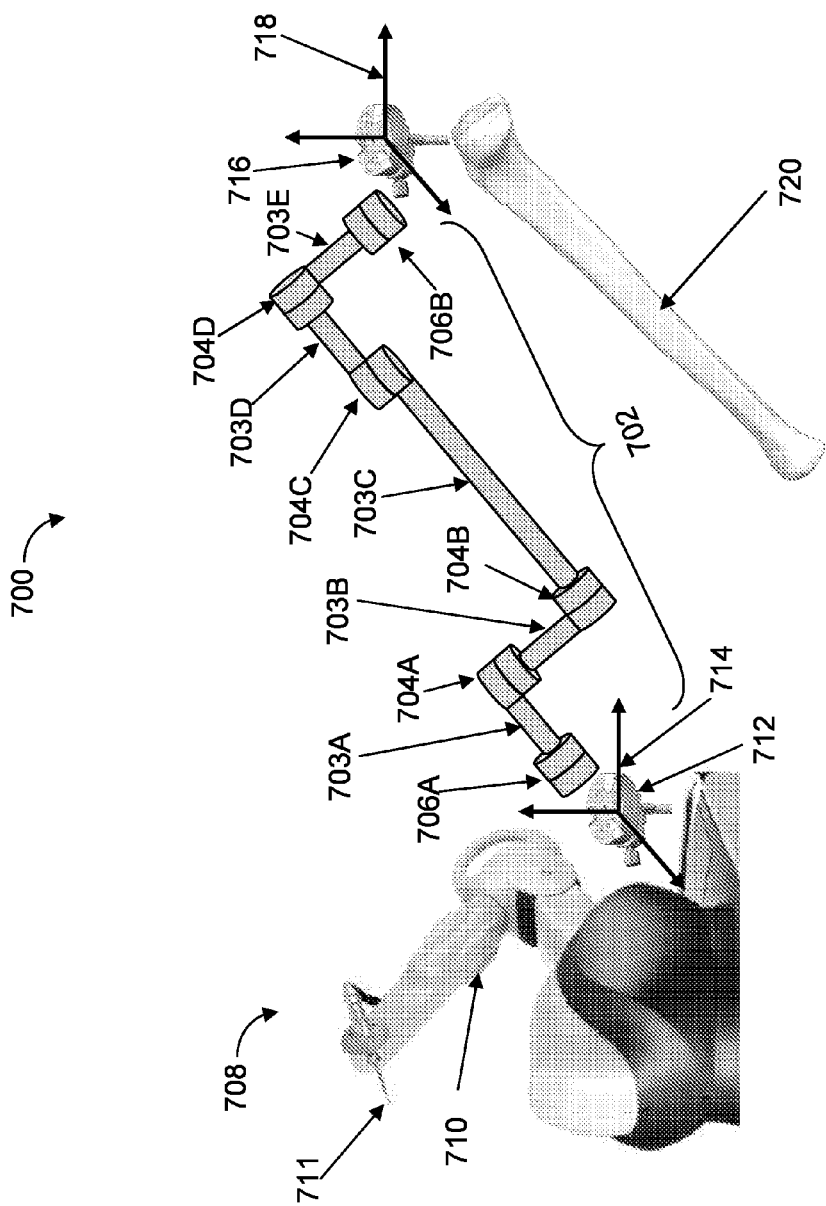
FIG. 7 illustrates an exemplary diagram of an instrumented linkage for resetting inertially tracked objects.

FIG. 7 illustrates an exemplary diagram 700 of an instrumented linkage 702 for resetting inertially tracked objects. The instrumented linkage 702 includes links 703A, 703B, 703C, 703D and 703E (collectively links 703), joints 704A, 704B, 704C and 704D (collectively joints 704), and connection portions 706A and 706B (collectively connection portions 706). The diagram 700 includes a haptic device 708 that includes a robotic arm 710 and a first IMU 712 with a first coordinate frame 714. The diagram 700 also includes a second IMU 716 with a second coordinate frame 718 mounted to a bone 720 (e.g., a tibia or femur bone). The connection portion 706A is configured to connect to the first IMU 712 to achieve a first reproducible reference pose. The connection portion 706B is configured to connect to the second IMU 716 to achieve a second reproducible reference pose. Preferably, the connection portions 706A, 706B include kinematic couplings (e.g., as described above in connection with FIGS. 5A-5C) to couple to corresponding kinematic couplings of the first and second IMUs 712, 716, respectively. In this embodiment, the first reproducible reference pose is defined by the kinematic coupling between the connection portion 706A and the first IMU 712. Similarly, the second reproducible reference pose is defined by the kinematic coupling between the connection portion 706B and the second IMU 716. The first and second reproducible references poses may be the same or different, depending on factors such as the calibration of the kinematic couplings, the geometry of the objects being coupled, and the like.

In some examples, one end of the instrumented linkage 702 is mounted to an object rather than including a connection portion 706. For example, the instrumented linkage 702 can have a proximal end (the end comprising the connection portion 706A) affixed to the base of the haptic device 708 and a freely moveable distal end (the end comprising the connection portion 706B) such that the connection portion 706B can be repeatably coupled to the bone 720 of the patient (e.g., via the second IMU 716). In some examples, the proximal end may be affixed to any other suitable location (such as, for example, to a rail of an operating table, a leg holder, etc.).

Each joint 704 incorporates one or more position sensors (not shown) to track a pose of the instrumented linkage 702. The position sensors may include any suitable sensor, such as a joint encoder. In operation, as the ends of the instrumented linkage 702 move (or are manipulated), the links 703 and joints 704 move accordingly. Data from the position sensors (and appropriate software) and the known geometry of the links 703 are used to determine a pose of one end of the instrumented linkage 702 (e.g., the distal end) relative to the other end (e.g., the proximal end) of the instrumented linkage 702. In this manner, regardless of the actual pose of the first IMU 712 and the second IMU 716 in physical space, the instrumented linkage 702 can be manipulated to connect to the first and second IMUs 712, 716. Advantageously, the mechanical linkage 702 allows objects that can not be physically manipulated into a reproducible reference pose (e.g., like the reproducible reference pose 300 in FIG. 3) to still be placed into a reproducible reference pose. For example, the haptic device 708 may be repositioned during a procedure without having to be recalibrated to a bone motion tracking system. In some embodiments, connection portions 706 can similarly function as joints 704 (e.g., including positions sensors to track a pose of the instrumented linkage 702).

A predetermined transformation between the second IMU 716 and the bone 720 can be determined by registering the bone 720 to a three-dimensional model of the bone as described above with respect to FIG. 4. A predetermined transformation between the robotic arm 710 (or another portion of the haptic device 710, such as the end effector 711) and the first IMU 712 can be determined. For example, the robotic arm 710 can include a number of links and joints similar to those of the instrumented linkage 702 so the pose of the end effector 711 can be calculated. A predetermined transformation can be calculated between the first IMU 712 and the end effector 711 based on the robotic arm 710. In some examples, the first IMU 712 is mounted to a different location of the haptic device 708 (e.g., to the end effector 711 of the robotic arm 710).

Figure 8:
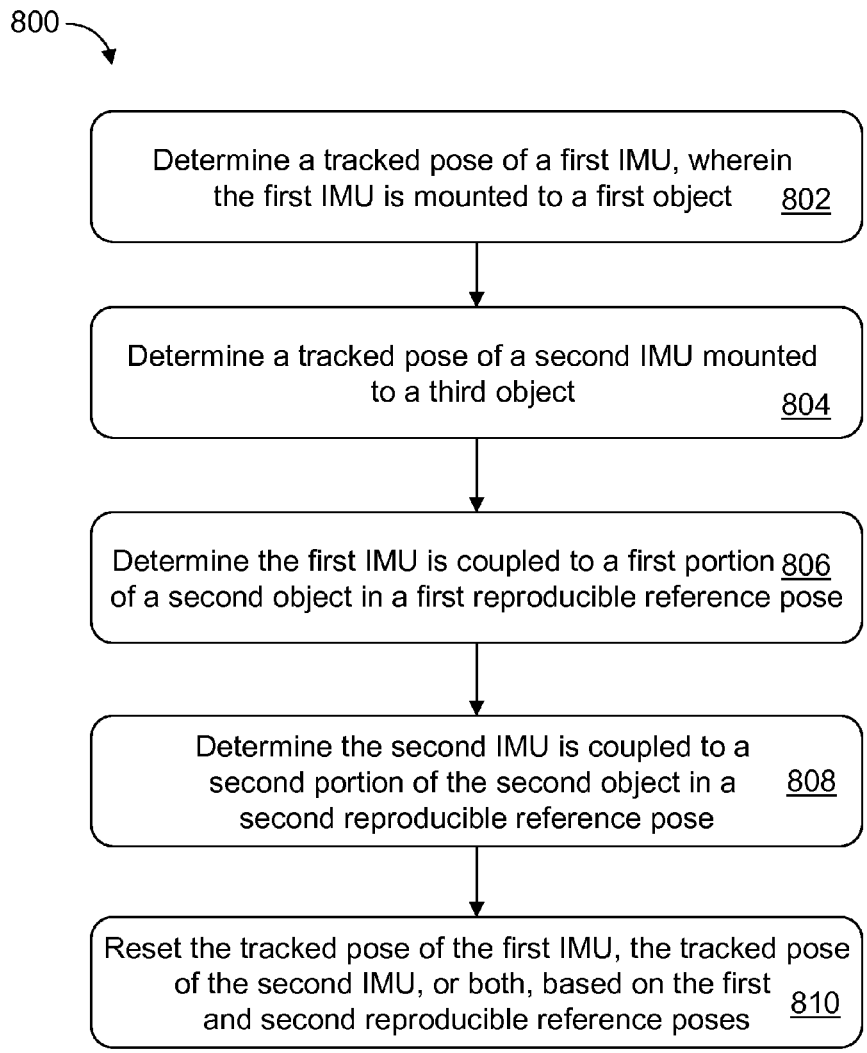
FIG. 8 illustrates an exemplary computer implemented method for resetting inertially tracked objects with an instrumented linkage.

FIG. 8 illustrates an exemplary computer implemented method 800 for resetting inertially tracked objects with an instrumented linkage (e.g., the instrumented linkage 702 in FIG. 7). This embodiment includes a first object (e.g., the haptic device 708), a second object (e.g., the instrumented linkage 702), and a third object (e.g., the bone 720), where a first IMU is mounted to the first object and a second IMU is mounted to the third object. At step 802, the inertial tracking system determines a tracked pose of the first IMU (e.g., the first IMU 712) that is mounted to the first object (e.g., the haptic device 708). At step 804, the inertial tracking system determines a tracked pose of the second IMU (e.g., the second IMU 716) that is mounted to the third object (e.g., the bone 720). At step 806, the inertial tracking system determines the first IMU is coupled to a first portion of the second object in a first reproducible reference pose (e.g., the first IMU 712 is coupled to the connection portion 706A of the instrumented linkage 702). At step 808, the inertial tracking system determines the second IMU is coupled to a second portion of the second object in a second reproducible reference pose (e.g., the second IMU 716 is coupled to the connection portion 706B). At step 810, the tracked pose of the inertial tracking system resets the tracked pose of the first IMU, the tracked pose of the second IMU, or both, based on the first reproducible reference pose and the second reproducible reference pose.

Referring to steps 806 and 808, the inertial tracking system can determine the IMUs are coupled to the respective portions of the second object using kinematic couplings as described above with reference to FIGS. 5A-5C. Referring to step 810, the inertial tracking system can use signals for the instrumented linkage 702 (e.g., joint 704 encoder signals) and the known geometry of the links 703 to determine the transformation between the first IMU 712 and the second IMU 716. As described above in connection with step 606 of FIG. 6, the inertial tracking system can determine that an error associated with the first IMU 712 and/or the second IMU 716 is above a predetermined threshold.

A transformation between the robotic arm 710 and the second IMU 716 can be determined. For example, a transformation between the end effector 711 and the second IMU 716 can be determined prior to the surgical procedure. In some embodiments, the location of the base of the robotic arm 710 and the second IMU 716 is determined using the first IMU 712. The robotic arm 710 may be used to register the patient's anatomy (e.g., instead of the probe as described above with reference to FIGS. 2-4). For example, the user may use the robotic arm 710 to register the bone 720. Registration may be accomplished, for example, by pointing a tip (e.g., a probe) of the distal end of the robotic arm 710 to anatomical landmarks on the bone 720 and/or by touching points on (or "painting") a surface of the bone 720 with the tip of the distal end of the robotic arm 710. As the user touches landmarks on the bone 720 and/or paints a surface of the bone 720, the surgical system (e.g., the surgical system 10 of FIG. 1) acquires data from the position sensors in the robotic arm 710 and determines a pose of the tip of the robotic arm 710. Simultaneously, the second IMU 716 provides data regarding motion of the bone 720 so that the surgical system can account for bone motion during registration. Based on the bone motion data and knowledge of the position of the tip of the robotic arm 710, the surgical system 10 is able to register the bone to diagnostic images and/or an anatomical model of the patient's anatomy (e.g., stored in the computing system 20). As described above with reference to FIGS. 7-8, the robotic arm 710 can be reregistered throughout a surgical procedure using the instrumented linkage 702.

Figure 9A:
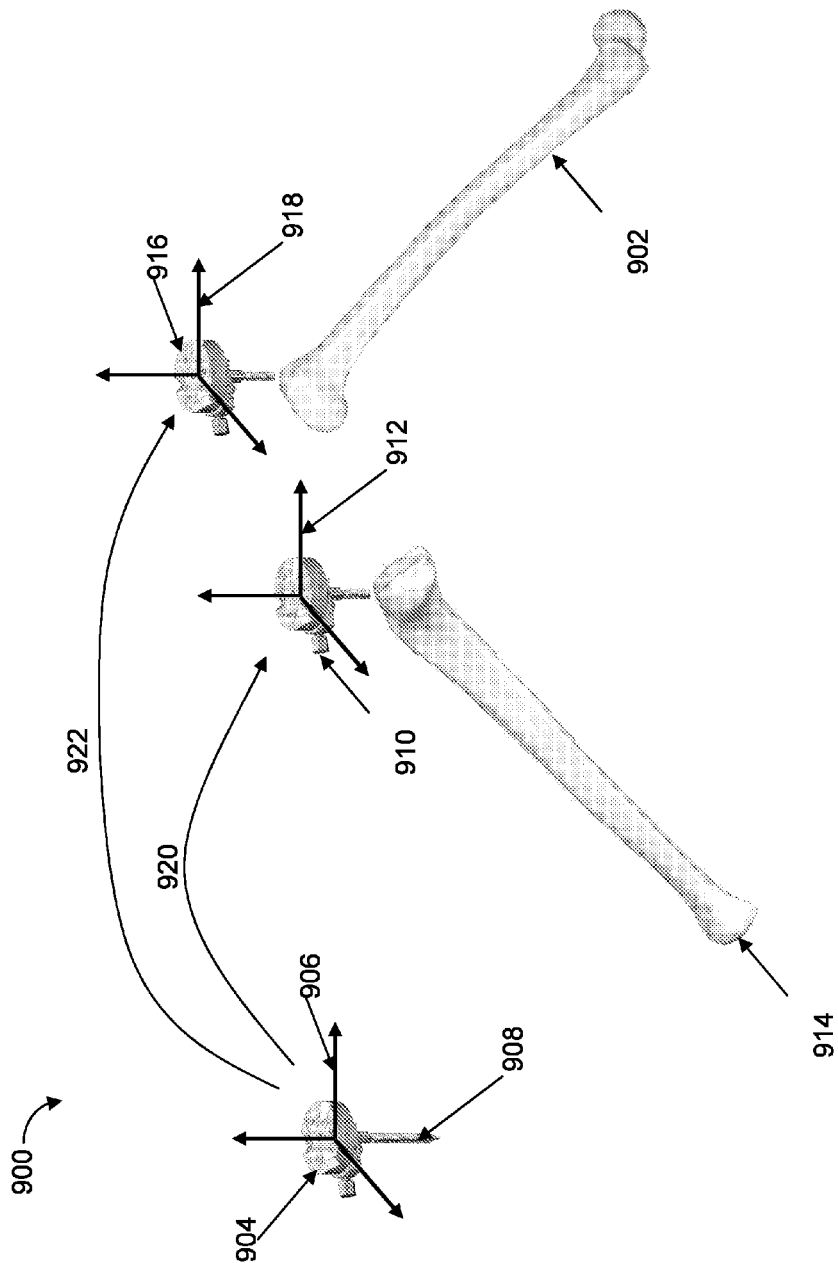
FIGS. 9A-9B illustrate exemplary diagrams of a first inertially tracked object being used to reset a second inertially tracked object, a third inertially tracked object, or both.
Figure 9B:
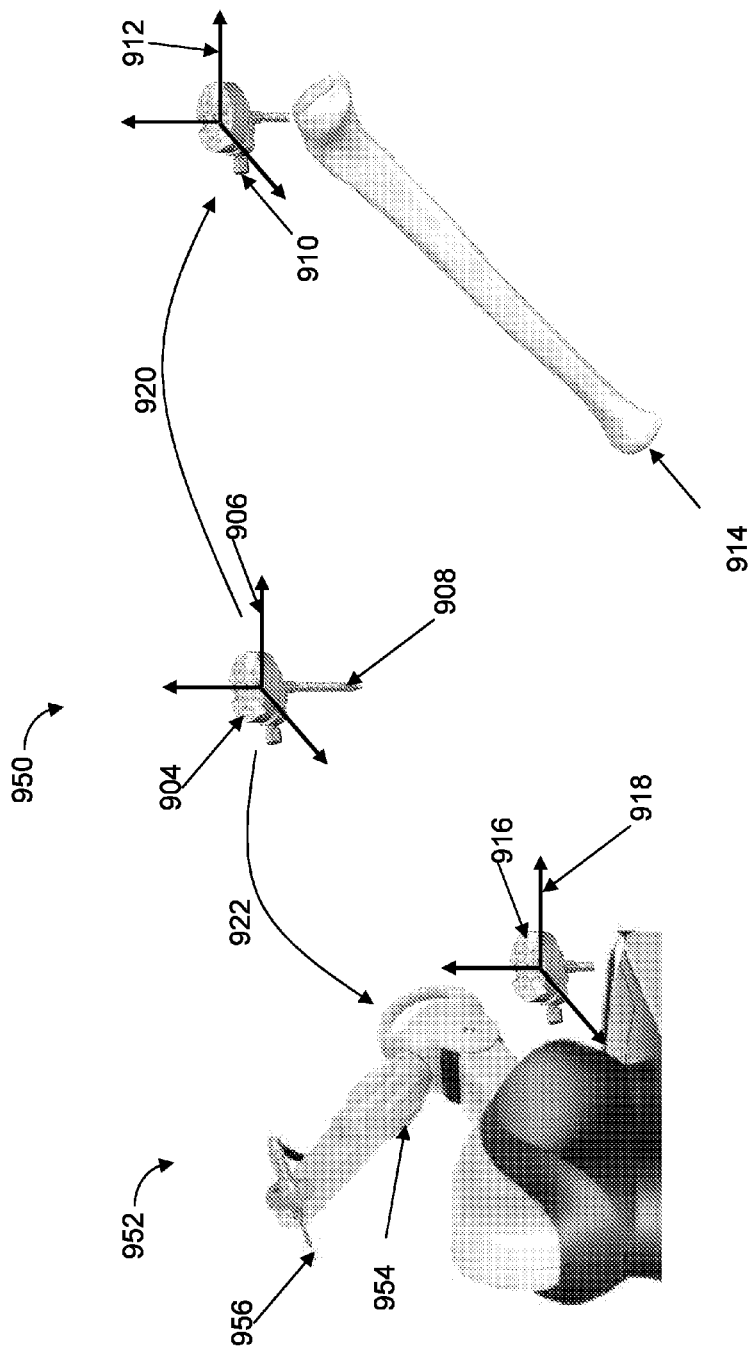

FIGS. 9A-9B illustrate exemplary diagrams 900, 950 of a first inertially tracked object (e.g., a first IMU 904 disposed on a probe 908) being used to reset a second inertially tracked object (e.g., a second IMU 910 disposed on a bone 914), a third inertially tracked object (e.g., a third IMU 916 disposed on a bone 902 or a haptic device 952), or both. The third object in FIG. 9A is different from the third object in FIG. 9B. FIG. 9A includes the bone 902 (e.g., a femur) as the third object. In contrast, FIG. 9B includes the haptic device 952 as the third object. Similar to FIG. 7, the haptic device 952 includes a robotic arm 954 and an end effector 956. With the exception of the different third objects, FIGS. 9A and 9B include the same remaining features and thus the following description is generally applicable and refers to either of the diagrams 900 or 950. A first IMU 904 with a coordinate frame 906 is mounted to the first object, the probe 908. A second IMU 910 with a coordinate frame 912 is mounted to the second object, the bone 914 (e.g., a tibia). A third IMU 916 with a coordinate frame 918 is mounted to the third object (either the bone 902 of FIG. 9A or the haptic device 952 of FIG. 9B). As indicated by arrow 920, the first IMU 904 can be placed in a first reproducible reference pose with the second IMU 910. As indicated by arrow 922, the first IMU 904 can be placed in a second reproducible reference pose with the third IMU 916.

Figure 10:
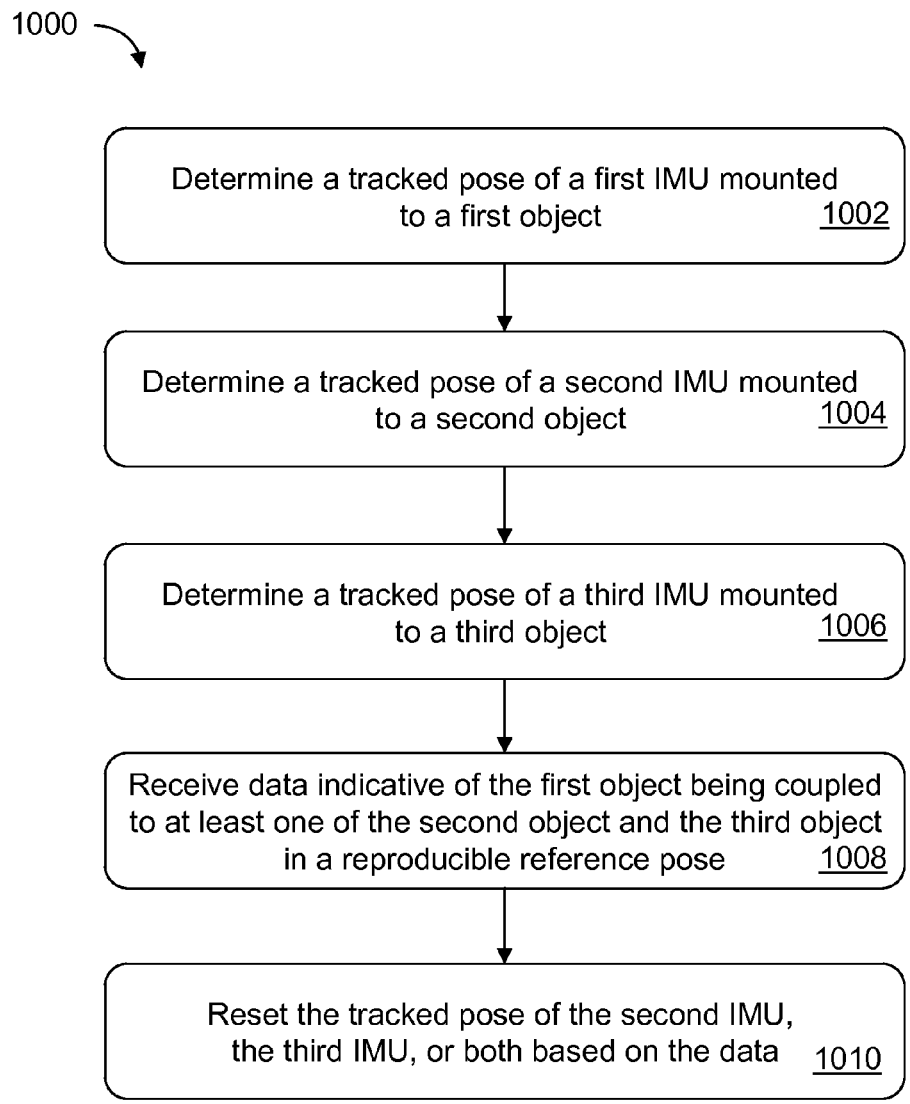
FIG. 10 illustrates an exemplary computer implemented method for using a first inertially tracked object to reset a second inertially tracked object, a third inertially tracked object, or both.

FIG. 10 illustrates an exemplary computer implemented method 1000 for using a first inertially tracked object to reset a second inertially tracked object, a third inertially tracked object, or both. In this embodiment, at step 1002, the inertial tracking system determines a tracked pose of a first IMU mounted to a first object (e.g., the first IMU 904 mounted to the probe 908). At step 1004, the inertial tracking system determines a tracked pose of a second IMU mounted to a second object (e.g., the second IMU 910 mounted to the bone 914). At step 1006, the inertial tracking system determines a tracked pose of a third IMU mounted to a third object (e.g., the third IMU 916 mounted to the bone 902 in FIG. 9A or the haptic device 952 in FIG. 9B). At step 1008, the inertial tracking system receives data indicative of the first object being coupled to at least one of the second object and the third object in a reproducible reference pose, for example, as indicated by arrows 920 (a first reproducible reference pose) and 922 (a second reproducible reference pose). At step 1010, the inertial tracking system resets the tracked pose of the second IMU, the third IMU, or both based on the data.

Referring to step 1008, the first object can be used to register the second object and/or the third object. Referring to FIG. 9A, for example, the probe 908 can be used to register the bone 902 and the bone 914. A predetermined transformation between the second IMU 910 and the bone 914 can be determined by registering the bone 914 to a three-dimensional model of the bone as described above with respect to FIG. 4. Similarly, a predetermined transformation between the third IMU 916 and the bone 914 can be determined by registering the bone 902 to a three-dimensional model of the bone. Advantageously, the predetermined transformation can map the object to the coordinate frame of the IMU mounted to the object (e.g., bone 914 to the coordinate frame 912 of the second IMU 910).

Further referring to step 1008, the first object can be used to reset the tracked pose of the second object and/or the third object. The inertial tracking system can determine an error associated with the second object and/or the third object exceeds a predetermined threshold. For example, referring to FIGS. 9A and 9B, the inertial tracking system can determine that an error associated with the second IMU 910 and/or the third IMU 916 exceeds a predetermined threshold (e.g., similar to step 606 of FIG. 6). The first object can be placed into the first reproducible reference pose with the second object to reset the tracked pose of the second object and/or the first object can be placed into the second reproducible reference pose with the third object to reset the tracked pose of the third object. The first object can include a first coupling configured to couple to a second coupling mounted to the second object to achieve the first reproducible reference pose. For example, the first IMU 904 and the probe 908 can be placed into the first reproducible reference pose with the bone 914 and the second IMU 910 as indicated by arrow 920 (e.g., using a kinematic coupling). Similarly, the first IMU 904 and the probe 908 can be placed into the second reproducible reference pose with the bone 902 and the third IMU 916 as shown by arrow 922. Referring to step 1008, the inertial tracking system can use the data (e.g., information indicative of the first reproducible reference pose, information indicative of the second reproducible reference pose, and/or tracking information of the objects) to reset the tracked pose of the first IMU, the second IMU, and/or the third IMU.

Referring further to steps 1008 and 1010, the first object can be used to locate the origin of the second object with respect to the third object. For example, referring to FIG. 9B, the first IMU 904 can be placed into a first reproducible reference pose with the second IMU 910 as indicated by arrow 920. The first IMU 904 can be placed into a second reproducible reference pose with the third IMU 916 as indicated by arrow 922. The inertial tracking system can receive data indicative of the first and second reproducible reference poses and use the data to determine the pose of the haptic device 952 with respect to the bone 914. For example, the inertial tracking system can use the data to calculate an origin of the base of the robotic arm 954 with respect to the bone 914. As another example, alternative tracking technologies can be used to estimate the transformation between the robotic arm 954 with respect to the bone 914. Such tracking systems can include optical, mechanical, fiber optic, and/or electromagnetic tracking systems (e.g., the instrumented linkage described with respect to FIGS. 7 and 8).

Another embodiment is similar to the embodiment of FIG. 9A described above except the second object is a second probe instead of the bone 914. For example, the first object (e.g., the probe 908) could be a blunt probe and the second object (e.g., the second probe (not shown)) could be a sharp probe. Either the blunt probe and/or the sharp probe could couple with the third object (e.g., the bone 902) to achieve a reproducible reference pose to reset the third IMU (e.g., the third IMU 916). In this embodiment, an exemplary computer implemented method for using a first inertially tracked object and/or a second inertially tracked object to reset a third inertially tracked object includes the following steps. The inertial tracking system determines a tracked pose of a first IMU mounted to a first object (e.g., the first IMU 904 mounted to the probe 908), a tracked pose of a second IMU mounted to a second object (e.g., the second IMU 910 mounted to the second probe), and a tracked pose of a third IMU mounted to a third object (e.g., the third IMU 916 mounted to the bone 902). The first and second objects are configured to couple in a first reproducible reference pose, and the third object is configured to couple to the first object and/or the second object in a second reproducible reference pose (e.g., using kinematic couplings as described in connection with FIGS. 5A-5C). The inertial tracking system receives data indicative of the third object being coupled to at least one of the first object and the second object in the second reproducible reference pose and resets the tracked pose of the third IMU mounted to the third object based on the data.

While embodiments have described the tracking system as being an inertial tracking system, the tracking system may additionally include other non-mechanical and/or mechanical tracking systems. The non-mechanical tracking system may include, for example, an optical (or visual), electromagnetic, radio, or acoustic tracking system, as is well known. The mechanical tracking system may include, for example, a fiber optic tracking system or an articulated arm having joint encoders) as described, for example, in U.S. Patent Application Pub. No. 2009/0314925, published Dec. 29, 2009, and U.S. Pat. No. 6,322,567, respectively, each of which is hereby incorporated by reference herein in its entirety. In one embodiment, the tracking system includes a mechanical tracking system having a jointed mechanical arm (e.g., an articulated arm having six or more degrees of freedom) adapted to track a bone of the patient.

The above-described systems and methods can be implemented in digital electronic circuitry, in computer hardware, firmware, and/or software. The implementation can be as a computer program product (i.e., a computer program tangibly embodied in an information carrier). The implementation can, for example, be in a machine-readable storage device, for execution by, or to control the operation of, data processing apparatus. The implementation can, for example, be a programmable processor, a computer, and/or multiple computers.

A computer program can be written in any form of programming language, including compiled and/or interpreted languages, and the computer program can be deployed in any form, including as a stand-alone program or as a subroutine, element, and/or other unit suitable for use in a computing environment. A computer program can be deployed to be executed on one computer or on multiple computers at one site.

Method steps can be performed by one or more programmable processors executing a computer program to perform functions of the invention by operating on input data and generating output. Method steps can also be performed by and an apparatus can be implemented as special purpose logic circuitry. The circuitry can, for example, be a FPGA (field programmable gate array) and/or an ASIC (application-specific integrated circuit). Modules, subroutines, and software agents can refer to portions of the computer program, the processor, the special circuitry, software, and/or hardware that implements that functionality.

Processors suitable for the execution of a computer program include, by way of example, both general and special purpose microprocessors, and any one or more processors of any kind of digital computer. Generally, a processor receives instructions and data from a read-only memory or a random access memory or both. The essential elements of a computer are a processor for executing instructions and one or more memory devices for storing instructions and data. Generally, a computer can include, can be operatively coupled to receive data from and/or transfer data to one or more mass storage devices for storing data (e.g., magnetic, magneto-optical disks, or optical disks).

Data transmission and instructions can also occur over a communications network. Information carriers suitable for embodying computer program instructions and data include all forms of non-volatile memory, including by way of example semiconductor memory devices. The information carriers can, for example, be EPROM, EEPROM, flash memory devices, magnetic disks, internal hard disks, removable disks, magneto-optical disks, CD-ROM, and/or DVD-ROM disks. The processor and the memory can be supplemented by, and/or incorporated in special purpose logic circuitry.

To provide for interaction with a user, the above described techniques can be implemented on a computer having a display device. The display device can, for example, be a cathode ray tube (CRT) and/or a liquid crystal display (LCD) monitor. The interaction with a user can, for example, be a display of information to the user and a keyboard and a pointing device (e.g., a mouse or a trackball) by which the user can provide input to the computer (e.g., interact with a user interface element). Other kinds of devices can be used to provide for interaction with a user. Other devices can, for example, be feedback provided to the user in any form of sensory feedback (e.g., visual feedback, auditory feedback, or tactile feedback). Input from the user can, for example, be received in any form, including acoustic, speech, and/or tactile input.

The above described techniques can be implemented in a distributed computing system that includes a back-end component. The back-end component can, for example, be a data server, a middleware component, and/or an application server. The above described techniques can be implemented in a distributing computing system that includes a front-end component. The front-end component can, for example, be a client computer having a graphical user interface, a Web browser through which a user can interact with an example implementation, and/or other graphical user interfaces for a transmitting device. The components of the system can be interconnected by any form or medium of digital data communication (e.g., a communication network). Examples of communication networks include a local area network (LAN), a wide area network (WAN), the Internet, wired networks, and/or wireless networks.

The system can include clients and servers. A client and a server are generally remote from each other and typically interact through a communication network. The relationship of client and server arises by virtue of computer programs running on the respective computers and having a client-server relationship to each other.

Packet-based networks can include, for example, the Internet, a carrier internet protocol (IP) network (e.g., local area network (LAN), wide area network (WAN), campus area network (CAN), metropolitan area network (MAN), home area network (HAN)), a private IP network, an IP private branch exchange (IPBX), a wireless network (e.g., radio access network (RAN), 802.11 network, 802.16 network, general packet radio service (GPRS) network, HiperLAN), and/or other packet-based networks. Circuit-based networks can include, for example, the public switched telephone network (PSTN), a private branch exchange (PBX), a wireless network (e.g., RAN, bluetooth, code-division multiple access (CDMA) network, time division multiple access (TDMA) network, global system for mobile communications (GSM) network), and/or other circuit-based networks.

The transmitting device can include, for example, a computer, a computer with a browser device, a telephone, an IP phone, a mobile device (e.g., cellular phone, personal digital assistant (PDA) device, laptop computer, electronic mail device), and/or other communication devices. The browser device includes, for example, a computer (e.g., desktop computer, laptop computer) with a world wide web browser (e.g., Microsoft® Internet Explorer® available from Microsoft Corporation, Mozilla® Firefox available from Mozilla Corporation). The mobile computing device includes, for example, a personal digital assistant (PDA).

Comprise, include, and/or plural forms of each are open ended and include the listed parts and can include additional parts that are not listed. And/or is open ended and includes one or more of the listed parts and combinations of the listed parts.

One skilled in the art will realize the invention may be embodied in other specific forms without departing from the spirit or essential characteristics thereof. The foregoing embodiments are therefore to be considered in all respects illustrative rather than limiting of the invention described herein. Scope of the invention is thus indicated by the appended claims, rather than by the foregoing description, and all changes that come within the meaning and range of equivalency of the claims are therefore intended to be embraced therein.

What is claimed is:

1. A method of initializing or resetting a tracking element, comprising:

initializing or resetting, by an inertial tracking system, an initial pose of a first inertial measurement unit (IMU) and a second IMU while the first and second IMUs are temporarily mechanically coupled together in a reproducible reference pose, wherein the initial poses of the first IMU and second IMU are known and achieved when the IMUs are coupled together in the reproducible reference pose;

determining, by the inertial tracking system, a tracked pose of the first (IMU), wherein the first IMU is mounted to a first object;

determining, by the inertial tracking system, a tracked pose of the second (IMU) relative to the first IMU wherein the second IMU is mounted to a second object; and resetting the initial pose of the first IMU and the second IMU, thereby eliminating drift caused over time between the tracked pose and the actual pose of the first IMU and second IMU, when the first IMU and the second IMU are returned to the reproducible reference pose.

2. The method of claim 1 wherein the first IMU comprises a first kinematic coupling and the second IMU comprises a second kinematic coupling.

3. The method of claim 2, wherein:
the first kinematic coupling is configured to kinematically couple to the second kinematic coupling to achieve the reference pose; and
initializing or resetting the tracked pose of the first IMU, initializing or resetting the tracked pose of the second IMU, or both, occurs when the second kinematic coupling is kinematically coupled to the first kinematic coupling.

4. The method of claim 2, wherein the tracked pose of the first IMU and the tracked pose of the second IMU are reset when the kinematic coupling on the first IMU is kinematically coupled to the kinematic coupling on the second IMU.

5. The method of claim 1:
wherein the step of initializing or resetting, by the inertial tracking system, the initial pose of the first and second IMU is automatically initiated by detecting when the first IMU is coupled to the second IMU in the reference pose.

6. The method of claim 5, wherein determining the first IMU and the second IMU are in the reference pose comprises determining the second IMU is kinematically coupled to the first IMU.

7. The method of claim 5 further comprising:
configuring a detection mechanism that includes a state indicator to indicate a coupling of the first and second IMUs based on the detection mechanism.

8. The method of claim 1, wherein the first IMU comprises a first coupling configured to couple to a second coupling mounted to the second object to achieve the reference pose.

9. The method of claim 1, wherein the reference pose comprises a predetermined transformation indicative of a first pose of the second IMU with respect to a first pose of the first IMU.

10. The method of claim 1 further comprising determining a tracked pose of the second IMU with respect to the first IMU based on the tracked pose of the first IMU, the tracked pose of the second IMU, and the reference pose.

11. The method of claim 1, further comprising:
determining, by the inertial tracking system, that an error associated with the first IMU, the second IMU, or both, exceeds a predetermined threshold; and
initializing or resetting the tracked pose of the first IMU, the tracked pose of the second IMU, or both, based on the reference pose.

12. The method of claim 1, further comprising:
a third object configured to couple to at least one of the first IMU and the second IMU to achieve a second reference pose;
receiving data indicative of the third object being coupled to the at least one of the first IMU and the second IMU in the second reference pose; and initializing or resetting a tracked pose of the first IMU or the second IMU coupled to the third object based on the data.

13. The method of claim 1 further comprising:
affixing a third IMU to the first object to track the first object.

14. The method of claim 1 further comprising:
configuring the first IMU to be kinematically coupled to the second IMU, wherein the kinematic coupling is a self-detecting kinematic assembly.

15. The method of claim 1 further comprising:
configuring a first coupling associated with the first IMU and a second coupling associated with the second IMU to be removably engaged together in a specific geometric configuration to achieve the reference pose.

16. The method of claim 1, wherein the first object and the second object are surgical instruments.

17. The method of claim 1, further comprising:
calculating a transform between the first IMU and the first object; and
calculating a transform between the second IMU and the second object.

18. The method of claim 1, further comprising:
using the tracked poses to track the first object coupled to the first IMU and the second object coupled to the second IMU as the first and second objects are moved independently.

19. A method of initializing or resetting a tracking element, comprising:
moving a first IMU and a second IMU into a reproducible reference pose, wherein the actual pose of the first IMU and the second IMU are known when in the reproducible reference pose;
setting an initial tracked pose of the first IMU and the second IMU when the IMUs are in the reproducible reference pose, such that the tracked poses of the IMUs correspond with the actual poses;
tracking the first IMU and the second IMU based on the initial tracked poses; and
returning the first IMU and the second IMU to the reproducible reference pose to eliminate draft occurring between the actual poses and the tracked poses since the previous setting of the initial tracked pose in the reproducible reference pose.

20. The method of claim 19, wherein the first IMU comprises a first repeatable coupling mechanism and wherein the second IMU comprises a second repeatable coupling mechanism;
wherein the first repeatable coupling mechanism is configured to engage with the second repeatable coupling mechanism; and
wherein moving the first IMU and the second IMU into the reproducible comprises engaging the first repeatable coupling mechanism with the second repeatable coupling mechanism.

21. A computer program product, tangibly embodied in a computer readable storage medium, the computer program product including instructions being operable to cause a data processing apparatus to:
initialize or reset, by an inertial tracking system, an initial pose of a first inertial measurement unit (IMU) and a second IMU while the first and second IMUs are temporarily mechanically coupled together in a reproducible reference pose, wherein the initial poses of the first IMU and second IMU are known and achieved when the IMUs are coupled together in the reproducible reference pose;

determine, by an inertial tracking system, a tracked pose of the first inertial measurement unit (IMU), wherein the first IMU is mounted to a first object;

determine, by an inertial tracking system, a tracked pose of the second (IMU) relative to the first IMU wherein the second IMU is mounted to a second object; and reset the initial pose of the first IMU and the second IMU, thereby eliminating drift caused over time between the tracked pose and the actual pose of the first IMU and second IMU, when the first IMU and the second IMU are returned to the reproducible reference pose.

* * * * *